US010322171B2

(12) United States Patent
Paessler et al.

(10) Patent No.: US 10,322,171 B2
(45) Date of Patent: Jun. 18, 2019

(54) VACCINE WITH REDUCED ENHANCEMENT OF VIRAL INFECTION

(71) Applicant: University of Texas Medical Branch at Galveston, Galveston, TX (US)

(72) Inventors: Slobodan Paessler, Galveston, TX (US); Veljko Veljkovic, Belgrade (RS)

(73) Assignee: THE BOARD OF REGENTS OF THE UNIVERSITY OF TEXAS SYSTEMS, Austin, TX (US)

( * ) Notice: Subject to any disclaimer, the term of this patent is extended or adjusted under 35 U.S.C. 154(b) by 0 days.

(21) Appl. No.: 15/437,101

(22) Filed: Feb. 20, 2017

(65) Prior Publication Data

US 2017/0312354 A1 Nov. 2, 2017

Related U.S. Application Data

(60) Provisional application No. 62/297,713, filed on Feb. 19, 2016.

(51) Int. Cl.

| | |
|---|---|
| ***A61K 39/12*** | (2006.01) |
| ***C07K 14/005*** | (2006.01) |
| ***C12N 7/00*** | (2006.01) |
| ***G06F 19/18*** | (2011.01) |
| *A61K 39/00* | (2006.01) |

(52) U.S. Cl.

CPC ............ *A61K 39/12* (2013.01); *C07K 14/005* (2013.01); *C12N 7/00* (2013.01); *G06F 19/18* (2013.01); *A61K 2039/5254* (2013.01); *C12N 2760/14122* (2013.01); *C12N 2760/14134* (2013.01); *C12N 2770/24122* (2013.01); *C12N 2770/24134* (2013.01); *Y02A 50/386* (2018.01); *Y02A 50/392* (2018.01)

(58) Field of Classification Search

None

See application file for complete search history.

(56) References Cited

U.S. PATENT DOCUMENTS

| | | | |
|---|---|---|---|
| 5,705,188 | A | 1/1998 | Junichi et al. |
| 9,267,947 | B2 | 2/2016 | Torres et al. |

FOREIGN PATENT DOCUMENTS

| | | |
|---|---|---|
| WO | 97/30731 | 8/1997 |

OTHER PUBLICATIONS

Dong and Liang, Virologica Sinica, 2018, 33:125-130. (Year: 2018).*

Paessler and Veljkovic, F1000Research 2018, 7:298, 11 pages. (Year: 2018).*

Pahil et al., PLoS One, 2017, 12(8):e0180505, 26 pages. (Year: 2018).*

Amemiya K, et al. "Interleukin-12 induces a Th1-like response to Burkholderia mallei and limited protection in BALB/c mice," Vaccine. Feb. 27, 2006;24(9)1413-20.

Amemiya K, et al. "Nonviable Burkholderia mallei induces a mixed Th1- and Th2-like cytokine response in BALB/c mice," Infect Immun. May 2002;70(5):2319-25.

Bandara AB, et al. "A disruption of ctpA encoding carboxy-terminal protease attenuates Burkholderia mallei and induces partial protection in CD1 mice," Microb Pathog. Sep. 2008;45(3):207-16.

Bondi SK, et al. "Strategies toward vaccines against Burkholderia mallei and Burkholderia pseudomallei," Expert Rev Vaccines. Nov. 2008;7(9):1357-65.

Brett PJ, et al. "Structural and immunological characterization of Burkholderia pseudomallei O-polysaccharide-flagellin protein conjugates," Infect Immun. Jul. 1996;64(7):2824-8.

Brett PJ, et al. "Isolation and characterization of Pseudomonas pseudomallei flagellin proteins," Infect Immun. May 1994;62(5):1914-9.

Bryan LE, et al. "Passive protection of diabetic rats with antisera specific for the polysaccharide portion of the lipopolysaccharide isolated from Pseudomonas pseudomallei," Can J Infect Dis. Jul. 1994;5(4):170-8.

Burtnick MN, et al. "The cluster 1 type VI secretion system is a major virulence determinant in Burkholderia pseudomallei," Infect Immun. Apr. 2011;79(4)1512-25.

Burtnick MN, et al. "Burkholderia mallei cluster 1 type VI secretion mutants exhibit growth and actin polymerization defects in RAW 264.7 murine macrophages," Infect Immun. Jan. 2010;78(1):88-99.

Choh LC, et al. "Burkholderia vaccines: are we moving forward?" Front Cell Infect Microbiol. Feb. 5, 2013;3:5.

Dance DA. "Melioidosis: the tip of the iceberg?" Clin Microbiol Rev. Jan. 1991;4(1):52-60.

Duval CW, et al. "The Histological Lesions of Experimental Glanders," J Exp Med. Jul. 17, 1907;9(4):352-80.

Galyov EE, et al. "Molecular insights into Burkholderia pseudomallei and Burkholderia mallei pathogenesis," Annu Rev Microbiol. 2010;64:495-517.

Horn JK. "Bacterial agents used for bioterrorism," Surg Infect (Larchmt). 2003 Fall;4(3):281-7.

Hornstra H, et al. "Molecular epidemiology of glanders, Pakistan," Emerg Infect Dis. Dec. 2009;15(12):2036-9.

Massey et al. "In vivo bioluminescence imaging of Burkholderia mallei respiratory infection and treatment in the mouse model." Frontiers in microbiology. Aug. 26, 2011;2:174.

Mott et al. "Characterization of the Burkholderia mallei tonB mutant and its potential as a backbone strain for vaccine development." PLoS neglected tropical diseases. Jun. 26, 2015;9(6):e0003863.

(Continued)

*Primary Examiner* — Stacy B Chen

(74) *Attorney, Agent, or Firm* — Rabin L. Teskin; LeClairRyan PLLC

(57) ABSTRACT

The present application generally relates to the development of a vaccine, or the production of antibodies, capable of providing improved protection against a virus associated with ADE, such as Zika, Dengue and Ebola, based on novel antigenic peptides identified using an informational spectrum method (ISM).

14 Claims, 12 Drawing Sheets

Figure 1B:
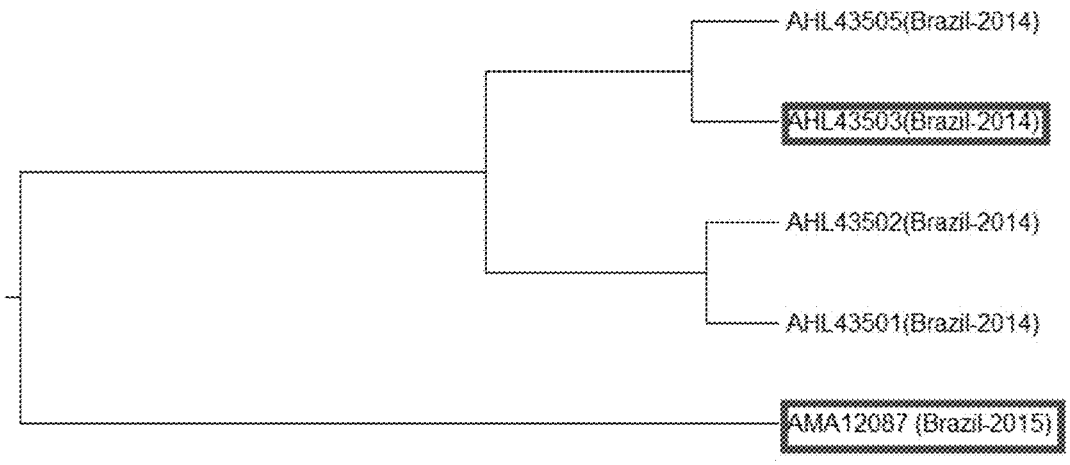

Specification includes a Sequence Listing.

(56) References Cited

OTHER PUBLICATIONS

Mougous et al. "A virulence locus of Pseudomonas aeruginosa encodes a protein secretion apparatus." Science. Jun. 9, 2006;312(5779):1526-30.
Nelson et al. "Evaluation of lipopolysaccharide and capsular polysaccharide as subunit vaccines against experimental melioidosis." Journal of medical microbiology. Dec. 1, 2004;53(12):1177-82.
Neubauer et al. "Serodiagnosis of Burkholderia mallei Infections in Horses: State-of-the-art and Perspectives." Journal of Veterinary Medicine, Series B. Jun. 2005;52(5):201-5.
Nieves et al. "A naturally derived outer-membrane vesicle vaccine protects against lethal pulmonary Burkholderia pseudomallei infection." Vaccine 29, 8381-8389 (2011).
Pukatzki et al. "Identification of a conserved bacterial protein secretion system in Vibrio cholerae using the Dictyostelium host model system." Proceedings of the National Academy of Sciences. Jan. 31, 2006;103(5):1528-33.
Sarkar-Tyson et al. "Progress toward development of vaccines against melioidosis: a review." Clinical therapeutics. Aug. 1, 2010;32(8):1437-45.
Schell et al. "Type VI secretion is a major virulence determinant in Burkholderia mallei." Molecular microbiology. Jun. 2007;64(6):1466-85.
Scholz et al. "Genotyping of Burkholderia mallei from an outbreak of glanders in Bahrain suggests multiple introduction events." PLoS neglected tropical diseases. Sep. 25, 2014;8(9):e3195.
Silva et al. "Development of Burkholderia mallei and pseudomallei vaccines." Frontiers in cellular and infection microbiology. Mar. 11, 2013;3:10.
Silva et al. "Correlates of immune protection following cutaneous immunization with an attenuated Burkholderia pseudomallei vaccine." Infection and immunity. Oct. 7, 2013:IAI-00915.
Srinivasan et al. "Glanders in a military research microbiologist." New England Journal of Medicine. Jul. 26, 2001;345(4):256-8.
Stone R. "Racing to defuse a bacterial time bomb." Science. Aug. 24, 2007;317(5841):1022-4.
Turner et al. "Construction and characterization of genetically definedaro omp mutants of Enterotoxigenic *Escherichia coli* and preliminary studies of safety and immunogenicity in humans." Infection and immunity. Aug. 1, 2001;69(8):4969-79.
Ulrich et al. "Aerogenic vaccination with a Burkholderia mallei auxotroph protects against aerosol-initiated glanders in mice." Vaccine. Mar. 14, 2005;23(16):1986-92.
Van Zandt KE. Glanders: an overview of infection in humans. Orphanet journal of rare diseases. Dec. 2013;8(1):131.
Verma, A.K. et al. Glanders: A re-emerging zoonotic disease: A review. Journal of Biological Sciences 14.1 (2014): 38-51.
Vollmer J, et al. "Characterization of three CpG oligodeoxynucleotide classes with distinct immunostimulatory activities," Eur J Immunol. Jan. 2004;34(1):251-62.
Wheelis M. "First shots fired in biological warfare," Nature. Sep. 17, 1998;395(6699):213.
Whitlock GC, et al. "Glanders: off to the races with Burkholderia mallei," FEMS Microbiol Lett. Dec. 2007;277(2):115-22.
Whitlock GC, et al. "Construction of a reporter system to study Burkholderia mallei type III secretion and identification of the BopA effector protein function in intracellular survival," Trans R Soc Trop Med Hyg. Dec. 2008;102 Suppl 1: S127-33.
Whitlock GC, et al. "Protective response to subunit vaccination against intranasal Burkholderia mallei and B. pseudomallei challenge," Procedia Vaccinol. 2010;2(1).

* cited by examiner

FIG 1A

>AHL43505(Brazil-2014)

FTCSKKMTGKSIQPENLEYRIMLSVHGSQHSGMIVNDIGHETDENRAKVEVTPNSPRAEATLGGFGSLGL
DCEPRTGLDFSDLYYLTMNNKHWLVHKEWFHDIPLPWHAGADTGTPHWNNKEALVEFKDAHAKRQTVVVL
GSQEGAVHTALAGALEAEMDGAKGRLFSGHLKCRLKMDKLRLKGVSYSLCTAAFTFTKVPAETLHGTVTV
EVQYAGTDGPCKVPAQMAVDMQTLTPVGRLITANPVITESTENSKMMLELDPPFGDSYIVIGVGDKKITH
HW(SEQ ID NO:1)

>AHL43503(Brazil-2014)

FTCCKKMPGKSIQPENLEYRIMLPVHGSQHSGMIVNDIGHETDENRAKVEVTPNSPRAEATLGGFGSLGL
DCEPRTGLDFSDLYYLTMNNKHWLVHKEWFHDIPLPWHAGADTGTPHWNNKEALVEFKDAHAKRQTVVVL
GSQEGAVHTALAGALEAEMDGAKGRLFSGHLKCRLKMDKLRLKGVSYSLCTAAFTFTKVPAETLHGTVTV
EVQSAGTDGPCKVPAQMAVDMQTLTPVGRLITANPVITESTENSKMMLELDPPFGDSYIVIGVGDKKITH
HW(SEQ ID NO:2)

>AHL43502(Brazil-2014)

FTCSKKMTGKSIQPENLEYRIMLSVHGSQHSGMIVNDIGHETDENRAKVEVTPNSPRAEATLGGFGSLGL
DCEPRTGLDFSDLYYLTMNNKHRLVRKEWFHDIPLPWHAGADTGTPHWNNKEALVEFKDAHAKRQTVVVL
GSQEGAVHTALAGALEAEMDGAKGRLFSGHLKCRLKMDKLRLKGVSYSLCTAAFTFTKVPAETLHGTVTV
EVQYAGTDGPCKVPAQMAVDMQTLTPVGRLITANPVITESTENSKMMLELDPPFGDSYIVIGVGDKKITH
HW(SEQ ID NO:3)

>AHL43501(Brazil-2014)

FTCSKKMTGKSIQPENLEYRIMLSVHGSQHSGMIVNDIGHETDENRAKVEVTPNSPRAEATLGGFGSLGL
DCEPRTGLDFSDLYYLTMNNKHWLVHKEWFHDIPLPWHAGADTGTPHWNNKEALVEFKDAHAKRQTVVVL
GSQEGAVHTALAGALEAEMDGAKGRLFSGHLKCRLKMDKLRLKGVSYSLCTAVCTAAKVPAETLHGTVTV
EVQYAGTDGPCKVPAQMAVDMQTLTPVGRLITANPVITESTENSKMMLELDPPFGDSYIVIGVGDKKITH
HW(SEQ ID NO:4)

>AMA12087 (Brazil-2015)

FACSKKMTGKSIQPENLEYRIMLSVHGSQHSGMIVNDTGHETDENRAKVEITPNSPRAEATLGGFGSLGL
DCEPRTGLDFSDLYYLTMNNKHWLVHKEWFHDIPLPWHAGADTGTPHWNNKEALVEFKDAHAKRQTVVVL
GSQEGAVHTALAGALEAEMDGAKGRLSSGHLKCRLKMDKLRLKGVSYSLCTAAFTFTKIPAETLHGTVTV
EVQYAGTDGPCKVPAQMAVDMQTLTPVGRLITANPVITESTENSKMMLELDPPFGDSYIVIGVGEKKITH
HW(SEQ ID NO:5)

FIG. 3C

(C)

The amino acid sequence of GP1 from Zika virus isolate AMA12087 (Brazil 2015) was modified to include the following amino acid substitutions:

D37I; D43L; D129L; D218L; and D266I

FACSKKMTGKSIQPENLEYRIMLSVHGSQHSGMIVNITGHETLENRAKVEITPNSPRAEA TLGGFGSLGLDCEPRTGLDFSDLYYLTMNNKHWLVHKEWFHDIPLPWHAGADTGTPH WNNKEALVEFKLAHAKRQTVVVLGSQEGAVHTALAGALEAEMDGAKGRLSSGHLKC RLKMDKLRLKGVSYSLCTAAFTFTKIPAETLHGTVTVEVQYAGTLGPCKVPAQMAVD MQTLTPVGRLITANPVITESTENSKMMLELDPPFGISYIVIGVGEKKITHHW (SEQ ID NO:19)

The amino acid sequence of GP1 from Zika virus isolate AHL43503 (Brazil 2014) was modified to include the following amino acid substitutions:

I21D; L175D; and L240D

FTCCKKMPGKSIQPENLEYRDMLPVHGSQHSGMIVNDIGHETDENRAKVEVTPNSPRAE ATLGGFGSLGLDCEPRTGLDFSDLYYLTMNNKHWLVHKEWFHDIPLPWHAGADTGTP HWNNKEALVEFKDAHAKRQTVVVLGSQEGAVHTALAGALEAEMDGAKGRLFSGHLK CRDKMDKLRLKGVSYSLCTAAFTFTKVPAETLHGTVTVEVQSAGTDGPCKVPAQMAV DMQTLTPVGRDITANPVITESTENSKMMLELDPPFGDSYIVIGVGDKKITHHW (SEQ ID NO:20)

FIG. 7A

(i) FACSKKMTGKSIQPENLEYRDMLSVHGSQHSGMIVNETGHETEENRAKVEITPNSPRAEATLGGFGS
LGLDCEPDTGLDFSDLYYLTMNNKHWLVHKEWFHDIPLPWHAGADTGTPHWNNKEALVEFKEAHAKRQTV
VVLGSQEGAVHTALAGALEAEMDGAKGRLSSGHLKCRDKMDKLRLKGVSYSLCTAAFTFTKIPAETLHGT
VTVEVQYAGTEGPCKVPAQMAVDMQTLTPVGRDITANPVITESTENSKMMLELDPPFGESYDVIGVGEKK
ITHHW (SEQ ID NO:7)

(ii) FACSKKMTGKSIQPENLEYRDMLSVHGSQHSGMIVNVTGHETIENRAKVEITPNSPRAEATLGGFG
SLGLDCEPTTGLDFSDLYYLTMNNKHWLVHKEWFHDIPLPWHAGADTGTPHWNNKEALVEFKLAHAKRQT
VVVLGSQEGAVHTALAGALEAEMDGAKGRLSSGHLKCRDKMDKLRLKGVSYSLCTAAFTFTKIPAETLHG
TVTVEVQYAGTEGPCKVPAQMAVDMQTLTPVGRFITANPVITESTENSKMMLELDPPFGGSYMVIGVGEK
KITHHW (SEQ ID NO:8)

(iii) FACSKKMTGKSIQPENLEYRMMLSVHGSQHSGMIVNVTGHETVENRAKVEITPNSPRAEATLGGF
GSLGLDCEPDTGLDFSDLYYLTMNNKHWLVHKEWFHDIPLPWHAGADTGTPHWNNKEALVEFKNAHAKRQ
TVVVLGSQEGAVHTALAGALEAEMDGAKGRLSSGHLKCRDKMDKLRLKGVSYSLCTAAFTFTKIPAETLH
GTVTVEVQYAGTVGPCKVPAQMAVDMQTLTPVGRSITANPVITESTENSKMMLELDPPFGNSYTVIGVGE
KKITHHW (SEQ ID NO:9)

(iv) FACSKKMTGKSIQPENLEYRFMLSVHGSQHSGMIVNNTGHETNENRAKVEITPNSPRAEATLGGFG
SLGLDCEPTTGLDFSDLYYLTMNNKHWLVHKEWFHDIPLPWHAGADTGTPHWNNKEALVEFKGAHAKRQT
VVVLGSQEGAVHTALAGALEAEMDGAKGRLSSGHLKCRDKMDKLRLKGVSYSLCTAAFTFTKIPAETLHG
TVTVEVQYAGTEGPCKVPAQMAVDMQTLTPVGRDITANPVITESTENSKMMLELDPPFGLSYRVIGVGEK
KITHHW (SEQ ID NO:10)

(v) FACSKKMTGKSIQPENLEYRRMLSVHGSQHSGMIVNITGHETIENRAKVEITPNSPRAEATLGGFGS
LGLDCEPRTGLDFSDLYYLTMNNKHWLVHKEWFHDIPLPWHAGADTGTPHWNNKEALVEFKIAHAKRQTV
VVLGSQEGAVHTALAGALEAEMDGAKGRLSSGHLKCRDKMDKLRLKGVSYSLCTAAFTFTKIPAETLHGT
VTVEVQYAGTIGPCKVPAQMAVDMQTLTPVGRRITANPVITESTENSKMMLELDPPFGISYRVIGVGEKK
ITHHW (SEQ ID NO:11)

(vi) FACSKKMTGKSIQPENLEYRMMLSVHGSQHSGMIVNNTGHETIENRAKVEITPNSPRAEATLGGFG
SLGLDCEPDTGLDFSDLYYLTMNNKHWLVHKEWFHDIPLPWHAGADTGTPHWNNKEALVEFKLAHAKRQT
VVVLGSQEGAVHTALAGALEAEMDGAKGRLSSGHLKCRDKMDKLRLKGVSYSLCTAAFTFTKIPAETLHG
TVTVEVQYAGTGGPCKVPAQMAVDMQTLTPVGRFITANPVITESTENSKMMLELDPPFGNSYDVIGVGEK
KITHHW (SEQ ID NO:12)

FIG. 7B

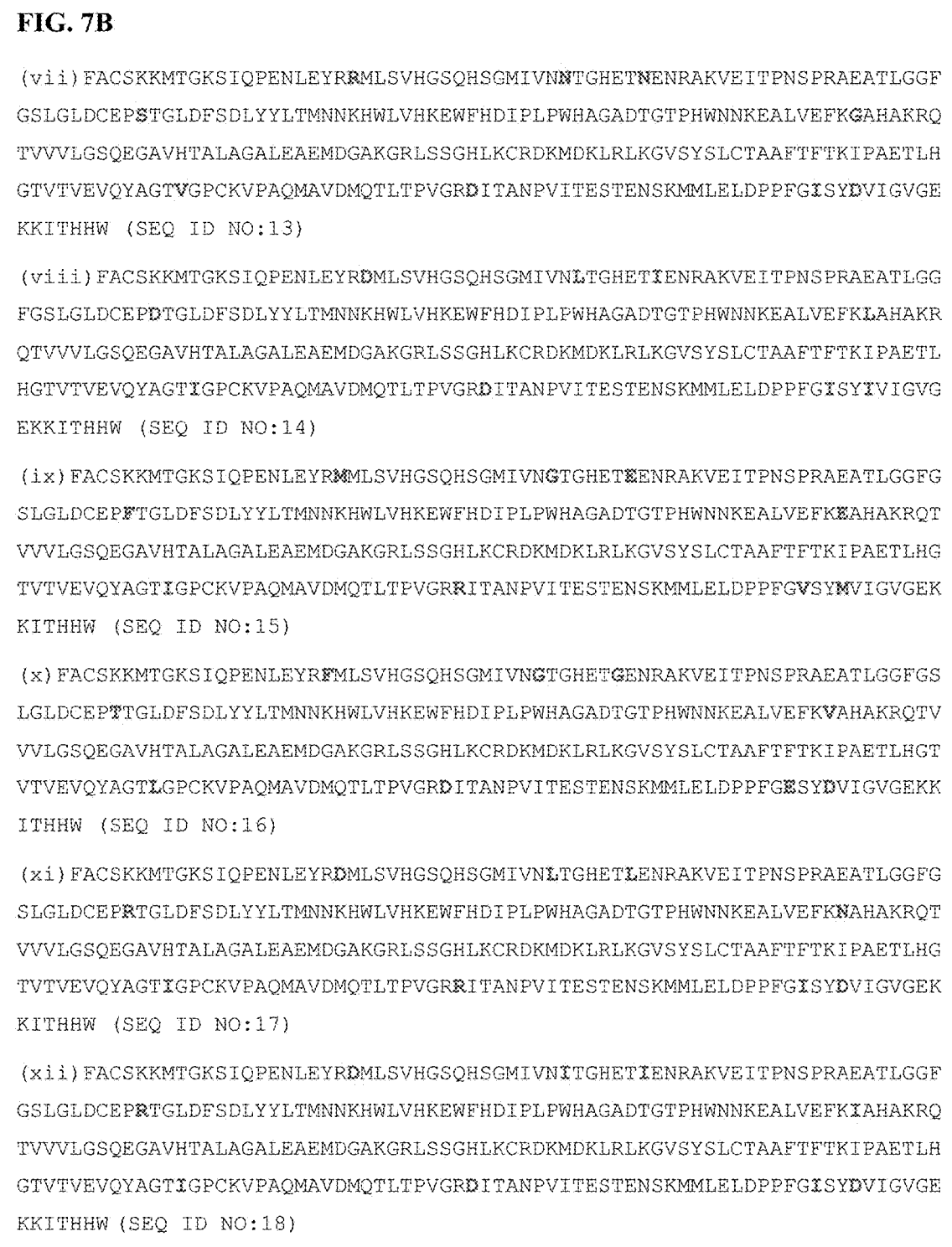

(vii) FACSKKMTGKSIQPENLEYRRMLSVHGSQHSGMIVNNTGHETNENRAKVEITPNSPRAEATLGGF GSLGLDCEPSTGLDFSDLYYLTMNNKHWLVHKEWFHDIPLPWHAGADTGTPHWNNKEALVEFKGAHAKRQ TVVVLGSQEGAVHTALAGALEAEMDGAKGRLSSGHLKCRDKMDKLRLKGVSYSLCTAAFTFTKIPAETLH GTVTVEVQYAGTVGPCKVPAQMAVDMQTLTPVGRDITANPVITESTENSKMMLELDPPFGISYDVIGVGE KKITHHW (SEQ ID NO:13)

(viii) FACSKKMTGKSIQPENLEYRDMLSVHGSQHSGMIVNLTGHETIENRAKVEITPNSPRAEATLGG FGSLGLDCEPDTGLDFSDLYYLTMNNKHWLVHKEWFHDIPLPWHAGADTGTPHWNNKEALVEFKLAHAKR QTVVVLGSQEGAVHTALAGALEAEMDGAKGRLSSGHLKCRDKMDKLRLKGVSYSLCTAAFTFTKIPAETL HGTVTVEVQYAGTIGPCKVPAQMAVDMQTLTPVGRDITANPVITESTENSKMMLELDPPFGISYIVIGVG EKKITHHW (SEQ ID NO:14)

(ix) FACSKKMTGKSIQPENLEYRMMLSVHGSQHSGMIVNGTGHETEENRAKVEITPNSPRAEATLGGFG SLGLDCEPFTGLDFSDLYYLTMNNKHWLVHKEWFHDIPLPWHAGADTGTPHWNNKEALVEFKEAHAKRQT VVVLGSQEGAVHTALAGALEAEMDGAKGRLSSGHLKCRDKMDKLRLKGVSYSLCTAAFTFTKIPAETLHG TVTVEVQYAGTIGPCKVPAQMAVDMQTLTPVGRRITANPVITESTENSKMMLELDPPFGVSYMVIGVGEK KITHHW (SEQ ID NO:15)

(x) FACSKKMTGKSIQPENLEYRFMLSVHGSQHSGMIVNGTGHETGENRAKVEITPNSPRAEATLGGFGS LGLDCEPTTGLDFSDLYYLTMNNKHWLVHKEWFHDIPLPWHAGADTGTPHWNNKEALVEFKVAHAKRQTV VVLGSQEGAVHTALAGALEAEMDGAKGRLSSGHLKCRDKMDKLRLKGVSYSLCTAAFTFTKIPAETLHGT VTVEVQYAGTLGPCKVPAQMAVDMQTLTPVGRDITANPVITESTENSKMMLELDPPFGESYDVIGVGEKK ITHHW (SEQ ID NO:16)

(xi) FACSKKMTGKSIQPENLEYRDMLSVHGSQHSGMIVNLTGHETLENRAKVEITPNSPRAEATLGGFG SLGLDCEPRTGLDFSDLYYLTMNNKHWLVHKEWFHDIPLPWHAGADTGTPHWNNKEALVEFKNAHAKRQT VVVLGSQEGAVHTALAGALEAEMDGAKGRLSSGHLKCRDKMDKLRLKGVSYSLCTAAFTFTKIPAETLHG TVTVEVQYAGTIGPCKVPAQMAVDMQTLTPVGRRITANPVITESTENSKMMLELDPPFGISYDVIGVGEK KITHHW (SEQ ID NO:17)

(xii) FACSKKMTGKSIQPENLEYRDMLSVHGSQHSGMIVNITGHETIENRAKVEITPNSPRAEATLGGF GSLGLDCEPRTGLDFSDLYYLTMNNKHWLVHKEWFHDIPLPWHAGADTGTPHWNNKEALVEFKIAHAKRQ TVVVLGSQEGAVHTALAGALEAEMDGAKGRLSSGHLKCRDKMDKLRLKGVSYSLCTAAFTFTKIPAETLH GTVTVEVQYAGTIGPCKVPAQMAVDMQTLTPVGRDITANPVITESTENSKMMLELDPPFGISYDVIGVGE KKITHHW (SEQ ID NO:18)

SEQUENCE LISTING

<160> NUMBER OF SEQ ID NOS: 20

<210> SEQ ID NO 1
<211> LENGTH: 282
<212> TYPE: PRT
<213> ORGANISM: Unknown
<220> FEATURE:
<223> OTHER INFORMATION: AHL43505(Brazil-2014)

<400> SEQUENCE: 1

Phe Thr Cys Ser Lys Lys Met Thr Gly Lys Ser Ile Gln Pro Glu Asn
1 5 10 15

Leu Glu Tyr Arg Ile Met Leu Ser Val His Gly Ser Gln His Ser Gly
20 25 30

Met Ile Val Asn Asp Ile Gly His Glu Thr Asp Glu Asn Arg Ala Lys
35 40 45

Val Glu Val Thr Pro Asn Ser Pro Arg Ala Glu Ala Thr Leu Gly Gly
50 55 60

Phe Gly Ser Leu Gly Leu Asp Cys Glu Pro Arg Thr Gly Leu Asp Phe
65 70 75 80

Ser Asp Leu Tyr Tyr Leu Thr Met Asn Asn Lys His Trp Leu Val His
85 90 95

Lys Glu Trp Phe His Asp Ile Pro Leu Pro Trp His Ala Gly Ala Asp
100 105 110

Thr Gly Thr Pro His Trp Asn Asn Lys Glu Ala Leu Val Glu Phe Lys
115 120 125

Asp Ala His Ala Lys Arg Gln Thr Val Val Val Leu Gly Ser Gln Glu
130 135 140

Gly Ala Val His Thr Ala Leu Ala Gly Ala Leu Glu Ala Glu Met Asp
145 150 155 160

Gly Ala Lys Gly Arg Leu Phe Ser Gly His Leu Lys Cys Arg Leu Lys
165 170 175

Met Asp Lys Leu Arg Leu Lys Gly Val Ser Tyr Ser Leu Cys Thr Ala
180 185 190

Ala Phe Thr Phe Thr Lys Val Pro Ala Glu Thr Leu His Gly Thr Val
195 200 205

Thr Val Glu Val Gln Tyr Ala Gly Thr Asp Gly Pro Cys Lys Val Pro
210 215 220

Ala Gln Met Ala Val Asp Met Gln Thr Leu Thr Pro Val Gly Arg Leu
225 230 235 240

Ile Thr Ala Asn Pro Val Ile Thr Glu Ser Thr Glu Asn Ser Lys Met
245 250 255

Met Leu Glu Leu Asp Pro Pro Phe Gly Asp Ser Tyr Ile Val Ile Gly
260 265 270

Val Gly Asp Lys Lys Ile Thr His His Trp
275 280

<210> SEQ ID NO 2
<211> LENGTH: 282
<212> TYPE: PRT
<213> ORGANISM: Unknown
<220> FEATURE:
<223> OTHER INFORMATION: Unknown - AHL43503(Brazil-2014)

<400> SEQUENCE: 2

Phe Thr Cys Cys Lys Lys Met Pro Gly Lys Ser Ile Gln Pro Glu Asn
1 5 10 15

-continued

```
Leu Glu Tyr Arg Ile Met Leu Pro Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Ser Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280


<210> SEQ ID NO 3
<211> LENGTH: 282
<212> TYPE: PRT
<213> ORGANISM: Unknown
<220> FEATURE:
<223> OTHER INFORMATION: AHL43502(Brazil-2014)

<400> SEQUENCE: 3

Phe Thr Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Arg Leu Val Arg
                85                  90                  95
```

-continued

```
Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280
```

<210> SEQ ID NO 4
<211> LENGTH: 282
<212> TYPE: PRT
<213> ORGANISM: Unknown
<220> FEATURE:
<223> OTHER INFORMATION: AHL43501(Brazil-2014)

<400> SEQUENCE: 4

```
Phe Thr Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Ile Gly His Glu Thr Asp Glu Asn Arg Ala Lys
        35                  40                  45

Val Glu Val Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Leu Lys
                165                 170                 175
```

-continued

```
Met Asp Lys Leu Arg Leu Lys Gly Val Ser Tyr Ser Leu Cys Thr Ala
            180                 185                 190

Val Cys Thr Ala Ala Lys Val Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280


<210> SEQ ID NO 5
<211> LENGTH: 282
<212> TYPE: PRT
<213> ORGANISM: Unknown
<220> FEATURE:
<223> OTHER INFORMATION: AMA12087 (Brazil-2015)

<400> SEQUENCE: 5

Phe Ala Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Asp Thr Gly His Glu Thr Asp Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asp Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Leu Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Asp Gly Pro Cys Lys Val Pro
    210                 215                 220

Ala Gln Met Ala Val Asp Met Gln Thr Leu Thr Pro Val Gly Arg Leu
225                 230                 235                 240

Ile Thr Ala Asn Pro Val Ile Thr Glu Ser Thr Glu Asn Ser Lys Met
                245                 250                 255
```

-continued

```
Met Leu Glu Leu Asp Pro Pro Phe Gly Asp Ser Tyr Ile Val Ile Gly
            260                 265                 270

Val Gly Glu Lys Lys Ile Thr His His Trp
        275                 280


<210> SEQ ID NO 6
<211> LENGTH: 676
<212> TYPE: PRT
<213> ORGANISM: Unknown
<220> FEATURE:
<223> OTHER INFORMATION: Viral Envelope Glycoprotein or Fragment

<400> SEQUENCE: 6

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Val Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Ala Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Gly Pro Lys Asn Ile Ser Gly
305                 310                 315                 320

Gln Ser Pro Ala Arg Thr Ser Ser Asp Pro Glu Thr Asn Thr Thr Asn
                325                 330                 335
```

-continued

```
Glu Asp His Lys Ile Met Ala Ser Glu Asn Ser Ser Ala Met Val Gln
            340                 345                 350

Val His Ser Gln Gly Arg Lys Ala Ala Val Ser His Leu Thr Thr Leu
        355                 360                 365

Ala Thr Ile Ser Thr Ser Pro Gln Pro Pro Thr Thr Lys Thr Gly Pro
    370                 375                 380

Asp Asn Ser Thr His Asn Thr Pro Val Tyr Lys Leu Asp Ile Ser Glu
385                 390                 395                 400

Ala Thr Gln Val Gly Gln His His Arg Arg Ala Asp Asn Asp Ser Thr
                405                 410                 415

Ala Ser Asp Thr Pro Pro Ala Thr Thr Ala Ala Gly Pro Leu Lys Ala
            420                 425                 430

Glu Asn Thr Asn Thr Ser Lys Ser Ala Asp Ser Leu Asp Leu Ala Thr
        435                 440                 445

Thr Thr Ser Pro Gln Asn Tyr Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Val Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Thr
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675


<210> SEQ ID NO 7
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 7

Phe Ala Cys Ser Lys Lys Met Thr Gly Lys Ser Ile Gln Pro Glu Asn
1               5                   10                  15
```

```
Leu Glu Tyr Arg Asp Met Leu Ser Val His Gly Ser Gln His Ser Gly
            20                  25                  30

Met Ile Val Asn Glu Thr Gly His Glu Thr Glu Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Asp Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Glu Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Glu Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Glu Ser Tyr Asp Val Ile Gly
            260                 265                 270

Val Gly Glu Lys Lys Ile Thr His His Trp
        275                 280


<210> SEQ ID NO 8
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 8

Phe Ala Cys Ser Lys Lys Met Thr Gly Lys Ser Ile Gln Pro Glu Asn
1               5                   10                  15

Leu Glu Tyr Arg Asp Met Leu Ser Val His Gly Ser Gln His Ser Gly
            20                  25                  30

Met Ile Val Asn Val Thr Gly His Glu Thr Ile Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Thr Thr Gly Leu Asp Phe
65                  70                  75                  80

Ser Asp Leu Tyr Tyr Leu Thr Met Asn Asn Lys His Trp Leu Val His
```

-continued

```
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Leu Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Glu Gly Pro Cys Lys Val Pro
    210                 215                 220

Ala Gln Met Ala Val Asp Met Gln Thr Leu Thr Pro Val Gly Arg Phe
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Gly Ser Tyr Met Val Ile Gly
            260                 265                 270

Val Gly Glu Lys Lys Ile Thr His His Trp
        275                 280


<210> SEQ ID NO 9
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 9

Phe Ala Cys Ser Lys Lys Met Thr Gly Lys Ser Ile Gln Pro Glu Asn
1               5                   10                  15

Leu Glu Tyr Arg Met Met Leu Ser Val His Gly Ser Gln His Ser Gly
            20                  25                  30

Met Ile Val Asn Val Thr Gly His Glu Thr Val Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Asp Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asn Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160
```

Gly Ala Lys Gly Arg Leu Ser Ser Gly His Leu Lys Cys Arg Asp Lys
165 170 175

Met Asp Lys Leu Arg Leu Lys Gly Val Ser Tyr Ser Leu Cys Thr Ala
180 185 190

Ala Phe Thr Phe Thr Lys Ile Pro Ala Glu Thr Leu His Gly Thr Val
195 200 205

Thr Val Glu Val Gln Tyr Ala Gly Thr Val Gly Pro Cys Lys Val Pro
210 215 220

Ala Gln Met Ala Val Asp Met Gln Thr Leu Thr Pro Val Gly Arg Ser
225 230 235 240

Ile Thr Ala Asn Pro Val Ile Thr Glu Ser Thr Glu Asn Ser Lys Met
245 250 255

Met Leu Glu Leu Asp Pro Pro Phe Gly Asn Ser Tyr Thr Val Ile Gly
260 265 270

Val Gly Glu Lys Lys Ile Thr His His Trp
275 280

<210> SEQ ID NO 10
<211> LENGTH: 282
<212> TYPE: PRT
<213> ORGANISM: Artificial
<220> FEATURE:
<223> OTHER INFORMATION: Modified Viral Envelope Glycoprotein or Fragment

<400> SEQUENCE: 10

Phe Ala Cys Ser Lys Lys Met Thr Gly Lys Ser Ile Gln Pro Glu Asn
1 5 10 15

Leu Glu Tyr Arg Phe Met Leu Ser Val His Gly Ser Gln His Ser Gly
20 25 30

Met Ile Val Asn Asn Thr Gly His Glu Thr Asn Glu Asn Arg Ala Lys
35 40 45

Val Glu Ile Thr Pro Asn Ser Pro Arg Ala Glu Ala Thr Leu Gly Gly
50 55 60

Phe Gly Ser Leu Gly Leu Asp Cys Glu Pro Thr Thr Gly Leu Asp Phe
65 70 75 80

Ser Asp Leu Tyr Tyr Leu Thr Met Asn Asn Lys His Trp Leu Val His
85 90 95

Lys Glu Trp Phe His Asp Ile Pro Leu Pro Trp His Ala Gly Ala Asp
100 105 110

Thr Gly Thr Pro His Trp Asn Asn Lys Glu Ala Leu Val Glu Phe Lys
115 120 125

Gly Ala His Ala Lys Arg Gln Thr Val Val Val Leu Gly Ser Gln Glu
130 135 140

Gly Ala Val His Thr Ala Leu Ala Gly Ala Leu Glu Ala Glu Met Asp
145 150 155 160

Gly Ala Lys Gly Arg Leu Ser Ser Gly His Leu Lys Cys Arg Asp Lys
165 170 175

Met Asp Lys Leu Arg Leu Lys Gly Val Ser Tyr Ser Leu Cys Thr Ala
180 185 190

Ala Phe Thr Phe Thr Lys Ile Pro Ala Glu Thr Leu His Gly Thr Val
195 200 205

Thr Val Glu Val Gln Tyr Ala Gly Thr Glu Gly Pro Cys Lys Val Pro
210 215 220

Ala Gln Met Ala Val Asp Met Gln Thr Leu Thr Pro Val Gly Arg Asp
225 230 235 240

-continued

```
Ile Thr Ala Asn Pro Val Ile Thr Glu Ser Thr Glu Asn Ser Lys Met
                245                 250                 255

Met Leu Glu Leu Asp Pro Pro Phe Gly Leu Ser Tyr Arg Val Ile Gly
            260                 265                 270

Val Gly Glu Lys Lys Ile Thr His His Trp
        275                 280


<210> SEQ ID NO 11
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 11

Phe Ala Cys Ser Lys Lys Met Thr Gly Lys Ser Ile Gln Pro Glu Asn
1               5                   10                  15

Leu Glu Tyr Arg Arg Met Leu Ser Val His Gly Ser Gln His Ser Gly
            20                  25                  30

Met Ile Val Asn Ile Thr Gly His Glu Thr Ile Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Ile Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Ile Gly Pro Cys Lys Val Pro
    210                 215                 220

Ala Gln Met Ala Val Asp Met Gln Thr Leu Thr Pro Val Gly Arg Arg
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Ile Ser Tyr Arg Val Ile Gly
            260                 265                 270

Val Gly Glu Lys Lys Ile Thr His His Trp
        275                 280


<210> SEQ ID NO 12
<211> LENGTH: 282
<212> TYPE: PRT
```

<213> ORGANISM: Artificial
<220> FEATURE:
<223> OTHER INFORMATION: Modified Viral Envelope Glycoprotein or Fragment

<400> SEQUENCE: 12

```
Phe Ala Cys Ser Lys Lys Met Thr Gly Lys Ser Ile Gln Pro Glu Asn
1               5                   10                  15

Leu Glu Tyr Arg Met Met Leu Ser Val His Gly Ser Gln His Ser Gly
            20                  25                  30

Met Ile Val Asn Asn Thr Gly His Glu Thr Ile Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Asp Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Leu Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Gly Gly Pro Cys Lys Val Pro
    210                 215                 220

Ala Gln Met Ala Val Asp Met Gln Thr Leu Thr Pro Val Gly Arg Phe
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asn Ser Tyr Asp Val Ile Gly
            260                 265                 270

Val Gly Glu Lys Lys Ile Thr His His Trp
        275                 280
```

<210> SEQ ID NO 13
<211> LENGTH: 282
<212> TYPE: PRT
<213> ORGANISM: Artificial
<220> FEATURE:
<223> OTHER INFORMATION: Modified Viral Envelope Glycoprotein or Fragment

<400> SEQUENCE: 13

```
Phe Ala Cys Ser Lys Lys Met Thr Gly Lys Ser Ile Gln Pro Glu Asn
1               5                   10                  15

Leu Glu Tyr Arg Arg Met Leu Ser Val His Gly Ser Gln His Ser Gly
            20                  25                  30

Met Ile Val Asn Asn Thr Gly His Glu Thr Asn Glu Asn Arg Ala Lys
```

-continued

```
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Ser Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Gly Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Val Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Ile Ser Tyr Asp Val Ile Gly
            260                 265                 270

Val Gly Glu Lys Lys Ile Thr His His Trp
        275                 280


<210> SEQ ID NO 14
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 14

Phe Ala Cys Ser Lys Lys Met Thr Gly Lys Ser Ile Gln Pro Glu Asn
1               5                   10                  15

Leu Glu Tyr Arg Asp Met Leu Ser Val His Gly Ser Gln His Ser Gly
            20                  25                  30

Met Ile Val Asn Leu Thr Gly His Glu Thr Ile Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Asp Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110
```

Thr Gly Thr Pro His Trp Asn Asn Lys Glu Ala Leu Val Glu Phe Lys
115 120 125

Leu Ala His Ala Lys Arg Gln Thr Val Val Val Leu Gly Ser Gln Glu
130 135 140

Gly Ala Val His Thr Ala Leu Ala Gly Ala Leu Glu Ala Glu Met Asp
145 150 155 160

Gly Ala Lys Gly Arg Leu Ser Ser Gly His Leu Lys Cys Arg Asp Lys
165 170 175

Met Asp Lys Leu Arg Leu Lys Gly Val Ser Tyr Ser Leu Cys Thr Ala
180 185 190

Ala Phe Thr Phe Thr Lys Ile Pro Ala Glu Thr Leu His Gly Thr Val
195 200 205

Thr Val Glu Val Gln Tyr Ala Gly Thr Ile Gly Pro Cys Lys Val Pro
210 215 220

Ala Gln Met Ala Val Asp Met Gln Thr Leu Thr Pro Val Gly Arg Asp
225 230 235 240

Ile Thr Ala Asn Pro Val Ile Thr Glu Ser Thr Glu Asn Ser Lys Met
245 250 255

Met Leu Glu Leu Asp Pro Pro Phe Gly Ile Ser Tyr Ile Val Ile Gly
260 265 270

Val Gly Glu Lys Lys Ile Thr His His Trp
275 280

<210> SEQ ID NO 15
<211> LENGTH: 282
<212> TYPE: PRT
<213> ORGANISM: Artificial
<220> FEATURE:
<223> OTHER INFORMATION: Modified Viral Envelope Glycoprotein or
Fragment

<400> SEQUENCE: 15

Phe Ala Cys Ser Lys Lys Met Thr Gly Lys Ser Ile Gln Pro Glu Asn
1 5 10 15

Leu Glu Tyr Arg Met Met Leu Ser Val His Gly Ser Gln His Ser Gly
20 25 30

Met Ile Val Asn Gly Thr Gly His Glu Thr Glu Glu Asn Arg Ala Lys
35 40 45

Val Glu Ile Thr Pro Asn Ser Pro Arg Ala Glu Ala Thr Leu Gly Gly
50 55 60

Phe Gly Ser Leu Gly Leu Asp Cys Glu Pro Phe Thr Gly Leu Asp Phe
65 70 75 80

Ser Asp Leu Tyr Tyr Leu Thr Met Asn Asn Lys His Trp Leu Val His
85 90 95

Lys Glu Trp Phe His Asp Ile Pro Leu Pro Trp His Ala Gly Ala Asp
100 105 110

Thr Gly Thr Pro His Trp Asn Asn Lys Glu Ala Leu Val Glu Phe Lys
115 120 125

Glu Ala His Ala Lys Arg Gln Thr Val Val Val Leu Gly Ser Gln Glu
130 135 140

Gly Ala Val His Thr Ala Leu Ala Gly Ala Leu Glu Ala Glu Met Asp
145 150 155 160

Gly Ala Lys Gly Arg Leu Ser Ser Gly His Leu Lys Cys Arg Asp Lys
165 170 175

Met Asp Lys Leu Arg Leu Lys Gly Val Ser Tyr Ser Leu Cys Thr Ala
180 185 190

Ala Phe Thr Phe Thr Lys Ile Pro Ala Glu Thr Leu His Gly Thr Val
        195                 200                 205

Thr Val Glu Val Gln Tyr Ala Gly Thr Ile Gly Pro Cys Lys Val Pro
    210                 215                 220

Ala Gln Met Ala Val Asp Met Gln Thr Leu Thr Pro Val Gly Arg Arg
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Val Ser Tyr Met Val Ile Gly
            260                 265                 270

Val Gly Glu Lys Lys Ile Thr His His Trp
        275                 280

<210> SEQ ID NO 16
<211> LENGTH: 282
<212> TYPE: PRT
<213> ORGANISM: Artificial
<220> FEATURE:
<223> OTHER INFORMATION: Modified Viral Envelope Glycoprotein or Fragment

<400> SEQUENCE: 16

Phe Ala Cys Ser Lys Lys Met Thr Gly Lys Ser Ile Gln Pro Glu Asn
1               5                   10                  15

Leu Glu Tyr Arg Phe Met Leu Ser Val His Gly Ser Gln His Ser Gly
            20                  25                  30

Met Ile Val Asn Gly Thr Gly His Glu Thr Gly Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Thr Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Val Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Leu Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Glu Ser Tyr Asp Val Ile Gly

```
            260                 265                 270

Val Gly Glu Lys Lys Ile Thr His His Trp
        275                 280


<210> SEQ ID NO 17
<211> LENGTH: 282
<212> TYPE: PRT
<213> ORGANISM: Artificial
<220> FEATURE:
<223> OTHER INFORMATION: Modified Viral Envelope Glycoprotein or
      Fragment

<400> SEQUENCE: 17

Phe Ala Cys Ser Lys Lys Met Thr Gly Lys Ser Ile Gln Pro Glu Asn
1               5                   10                  15

Leu Glu Tyr Arg Asp Met Leu Ser Val His Gly Ser Gln His Ser Gly
            20                  25                  30

Met Ile Val Asn Leu Thr Gly His Glu Thr Leu Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Asn Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Ile Gly Pro Cys Lys Val Pro
    210                 215                 220

Ala Gln Met Ala Val Asp Met Gln Thr Leu Thr Pro Val Gly Arg Arg
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Ile Ser Tyr Asp Val Ile Gly
            260                 265                 270

Val Gly Glu Lys Lys Ile Thr His His Trp
        275                 280


<210> SEQ ID NO 18
<211> LENGTH: 282
<212> TYPE: PRT
<213> ORGANISM: Artificial
<220> FEATURE:
<223> OTHER INFORMATION: Modified Viral Envelope Glycoprotein or
      Fragment
```

<400> SEQUENCE: 18

Phe Ala Cys Ser Lys Lys Met Thr Gly Lys Ser Ile Gln Pro Glu Asn
1               5                   10                  15

Leu Glu Tyr Arg Asp Met Leu Ser Val His Gly Ser Gln His Ser Gly
            20                  25                  30

Met Ile Val Asn Ile Thr Gly His Glu Thr Ile Glu Asn Arg Ala Lys
        35                  40                  45

Val Glu Ile Thr Pro Asn Ser Pro Arg Ala Glu Ala Thr Leu Gly Gly
    50                  55                  60

Phe Gly Ser Leu Gly Leu Asp Cys Glu Pro Arg Thr Gly Leu Asp Phe
65                  70                  75                  80

Ser Asp Leu Tyr Tyr Leu Thr Met Asn Asn Lys His Trp Leu Val His
                85                  90                  95

Lys Glu Trp Phe His Asp Ile Pro Leu Pro Trp His Ala Gly Ala Asp
            100                 105                 110

Thr Gly Thr Pro His Trp Asn Asn Lys Glu Ala Leu Val Glu Phe Lys
        115                 120                 125

Ile Ala His Ala Lys Arg Gln Thr Val Val Val Leu Gly Ser Gln Glu
    130                 135                 140

Gly Ala Val His Thr Ala Leu Ala Gly Ala Leu Glu Ala Glu Met Asp
145                 150                 155                 160

Gly Ala Lys Gly Arg Leu Ser Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Ile Pro Ala Glu Thr Leu His Gly Thr Val
        195                 200                 205

Thr Val Glu Val Gln Tyr Ala Gly Thr Ile Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Ile Ser Tyr Asp Val Ile Gly
            260                 265                 270

Val Gly Glu Lys Lys Ile Thr His His Trp
        275                 280

<210> SEQ ID NO 19
<211> LENGTH: 282
<212> TYPE: PRT
<213> ORGANISM: Artificial
<220> FEATURE:
<223> OTHER INFORMATION: Modified GP1 from virus isolate AMA12087
(Brazil 2015)

<400> SEQUENCE: 19

Phe Ala Cys Ser Lys Lys Met Thr Gly Lys Ser Ile Gln Pro Glu Asn
1               5                   10                  15

Leu Glu Tyr Arg Ile Met Leu Ser Val His Gly Ser Gln His Ser Gly
            20                  25                  30

Met Ile Val Asn Ile Thr Gly His Glu Thr Leu Glu Asn Arg Ala Lys
        35                  40                  45

Val Glu Ile Thr Pro Asn Ser Pro Arg Ala Glu Ala Thr Leu Gly Gly
    50                  55                  60

-continued

Phe Gly Ser Leu Gly Leu Asp Cys Glu Pro Arg Thr Gly Leu Asp Phe
65 70 75 80

Ser Asp Leu Tyr Tyr Leu Thr Met Asn Asn Lys His Trp Leu Val His
85 90 95

Lys Glu Trp Phe His Asp Ile Pro Leu Pro Trp His Ala Gly Ala Asp
100 105 110

Thr Gly Thr Pro His Trp Asn Asn Lys Glu Ala Leu Val Glu Phe Lys
115 120 125

Leu Ala His Ala Lys Arg Gln Thr Val Val Val Leu Gly Ser Gln Glu
130 135 140

Gly Ala Val His Thr Ala Leu Ala Gly Ala Leu Glu Ala Glu Met Asp
145 150 155 160

Gly Ala Lys Gly Arg Leu Ser Ser Gly His Leu Lys Cys Arg Leu Lys
165 170 175

Met Asp Lys Leu Arg Leu Lys Gly Val Ser Tyr Ser Leu Cys Thr Ala
180 185 190

Ala Phe Thr Phe Thr Lys Ile Pro Ala Glu Thr Leu His Gly Thr Val
195 200 205

Thr Val Glu Val Gln Tyr Ala Gly Thr Leu Gly Pro Cys Lys Val Pro
210 215 220

Ala Gln Met Ala Val Asp Met Gln Thr Leu Thr Pro Val Gly Arg Leu
225 230 235 240

Ile Thr Ala Asn Pro Val Ile Thr Glu Ser Thr Glu Asn Ser Lys Met
245 250 255

Met Leu Glu Leu Asp Pro Pro Phe Gly Ile Ser Tyr Ile Val Ile Gly
260 265 270

Val Gly Glu Lys Lys Ile Thr His His Trp
275 280

<210> SEQ ID NO 20
<211> LENGTH: 282
<212> TYPE: PRT
<213> ORGANISM: Artificial
<220> FEATURE:
<223> OTHER INFORMATION: GP1 from Zika virus isolate AHL43503 (Brazil 2014)

<400> SEQUENCE: 20

Phe Thr Cys Cys Lys Lys Met Pro Gly Lys Ser Ile Gln Pro Glu Asn
1 5 10 15

Leu Glu Tyr Arg Asp Met Leu Pro Val His Gly Ser Gln His Ser Gly
20 25 30

Met Ile Val Asn Asp Ile Gly His Glu Thr Asp Glu Asn Arg Ala Lys
35 40 45

Val Glu Val Thr Pro Asn Ser Pro Arg Ala Glu Ala Thr Leu Gly Gly
50 55 60

Phe Gly Ser Leu Gly Leu Asp Cys Glu Pro Arg Thr Gly Leu Asp Phe
65 70 75 80

Ser Asp Leu Tyr Tyr Leu Thr Met Asn Asn Lys His Trp Leu Val His
85 90 95

Lys Glu Trp Phe His Asp Ile Pro Leu Pro Trp His Ala Gly Ala Asp
100 105 110

Thr Gly Thr Pro His Trp Asn Asn Lys Glu Ala Leu Val Glu Phe Lys
115 120 125

Asp Ala His Ala Lys Arg Gln Thr Val Val Val Leu Gly Ser Gln Glu
130 135 140

-continued

```
Gly Ala Val His Thr Ala Leu Ala Gly Ala Leu Glu Ala Glu Met Asp
145                 150                 155                 160

Gly Ala Lys Gly Arg Leu Phe Ser Gly His Leu Lys Cys Arg Asp Lys
                165                 170                 175

Met Asp Lys Leu Arg Leu Lys Gly Val Ser Tyr Ser Leu Cys Thr Ala
            180                 185                 190

Ala Phe Thr Phe Thr Lys Val Pro Ala Glu Thr Leu His Gly Thr Val
        195                 200                 205

Thr Val Glu Val Gln Ser Ala Gly Thr Asp Gly Pro Cys Lys Val Pro
    210                 215                 220

Ala Gln Met Ala Val Asp Met Gln Thr Leu Thr Pro Val Gly Arg Asp
225                 230                 235                 240

Ile Thr Ala Asn Pro Val Ile Thr Glu Ser Thr Glu Asn Ser Lys Met
                245                 250                 255

Met Leu Glu Leu Asp Pro Pro Phe Gly Asp Ser Tyr Ile Val Ile Gly
            260                 265                 270

Val Gly Asp Lys Lys Ile Thr His His Trp
        275                 280
```

VACCINE WITH REDUCED ENHANCEMENT OF VIRAL INFECTION

This application claims priority to and benefit of U.S. Provisional Application No. 62/297,713 filed Feb. 19, 2016, the disclosures of which are herein incorporated by reference in their entirety.

SEQUENCE LISTING

This application includes as part of its disclosure a biological sequence listing text file named "49561o1204.txt" having a size of 54,202 bytes that was created Jul. 17, 2017, which is incorporated by reference in its entirety.

FIELD OF THE INVENTION

The invention generally relates to the development of a vaccine capable of providing protection against viral infection associated with antibody-dependent enhancement (ADE) of infection, such as Zika, Dengue and Ebola infections or other viruses where viral antigens may elicit ADE, as well as the production of antibodies to treat or prevent such infections. More particularly, the invention is related to the use of an information spectrum method (ISM) to identify novel peptides that possess sufficient structural homology with Zika envelope glycoprotein (GP1) to be suitable for use as an antigen to elicit an immune response, i.e., antibody production, but which elicit no or reduced activation of the complement system.

BACKGROUND OF THE INVENTION

Zika is a disease caused by Zika virus, which is spread to people primarily through the bite of an infected *Aedes* species mosquito. The most common symptoms of Zika are fever, rash, joint pain, and conjunctivitis. The illness is usually mild (not severe enough to require hospitalization or result in death), with symptoms appearing 2 to 7 days after being bitten by an infected mosquito and lasting for several days to a week. However, there have been reports of serious birth defects, namely microcephaly, and other poor pregnancy outcomes in babies of mothers who were infected with Zika virus while pregnant. There have also been cases of Guillain-Barré syndrome (GBS) reported in patients following suspected Zika virus infection. GBS is a rare disorder where a person's own immune system damages the nerve cells, causing muscle weakness and sometimes, paralysis. These symptoms can last anywhere from a few weeks to several months, although some people have permanent damage and, in rare cases, GBS may result in death.

Zika virus is a member of the virus family Flaviviridae, and is thus related to dengue, yellow fever, Japanese encephalitis, and West Nile viruses. Like other members of the *Flavivirus* genus, Zika contains a positive single-stranded genomic RNA, encoding a polyprotein that is processed into three structural proteins (the capsid (C), the precursor of membrane (prM) and the envelope (E)) and seven nonstructural proteins (NS1 to NS5).

Zika virus is transmitted to people primarily through the bite of an infected *Aedes* species mosquito (*A. aegypti* and *A. albopictus*). These are the same mosquitoes that spread dengue and chikungunya viruses. These mosquitoes typically lay eggs in and near standing water in things like buckets, bowls, animal dishes, flower pots and vases. They prefer to bite people, and live indoors and outdoors near people. Mosquitoes that spread chikungunya, dengue, and Zika are aggressive daytime biters. They can also bite at night. Mosquitoes become infected when they feed on a person already infected with the virus. Infected mosquitoes can then spread the virus to other people through bites. Zika virus usually remains in the blood of an infected person for about a week but it can be found longer in some people.

Prior to 2015, Zika virus outbreaks occurred in areas of Africa, Southeast Asia, and the Pacific Islands. The first human Zika infection was reported in Uganda in 1964 and the virus was later isolated from humans in South East Asia. Despite this broad geographical distribution, human Zika infections remained sporadic and limited to small-scale epidemics for decades, until 2007, when a large epidemic was reported on Yap Island, a territory of the Federated States of Micronesia, with nearly 75% of the population being infected with the virus. Moreover, an outbreak of a syndrome due to Zika fever was reported in French Polynesia, in addition to several cases of Zika infection in New Caledonia, Easter Island and the Cook Islands, indicating a rapid spreading of the virus in the Pacific. Two imported cases of Zika infection of travellers from Indonesia and the Cook Islands, respectively, to Australia and two from Thailand to Europe and Canada, respectively, was described recently (see, Kwong et al. (2013) Am J Trop Med Hyg 89:516-517 Tappe et al. (2014) European communicable disease bulletin; Pyke et al. (2014) PLoS currents 6; Fonseca et al. (2014) Am J Trop Med Hyg 91:1035-1038), emphasizing the capacity of Zika to spread to non-endemic areas where the proper mosquito vector might be present.

In May 2015, the Pan American Health Organization (PAHO) issued an alert regarding the first confirmed Zika virus infections in Brazil. Currently, outbreaks are occurring in many countries. Zika virus will continue to spread and it will be difficult to determine how and where the virus will spread over time.

On Jan. 22, 2016, the Centers for Disease Control and Prevention (CDC) activated its Emergency Operations Center (EOC) to respond to outbreaks of Zika occurring in the Americas and increased reports of birth defects and Guillain-Barré syndrome in areas affected by Zika.

In Feb. 1, 2016, the World Health Organization declared a Public Health Emergency of International Concern (PHEIC) because of clusters of microcephaly and other neurological disorders in some areas affected by Zika.

On Feb. 8, 2016, CDC elevated its EOC activation to a Level 1, the highest level.

As of Feb. 17, 2016, in the United States, 84 cases of travel-associated Zika virus disease cases have been reported. With the recent outbreaks, the number of Zika cases among travelers visiting or returning to the United States will likely increase. These imported cases could result in local spread of tile virus in the United States.

There is currently no available vaccine to prevent or treat Zika infection. Accordingly, the identification of novel antigens that are capable of eliciting an immune response against Zika to provide protection against infection is desirable.

SUMMARY OF THE INVENTION

The invention provides a method for identifying novel antigens possessing structural homology with the envelope glycoprotein (GP) from a virus associated with antibody-dependent enhancement (ADE) of infection, such as Flaviviridae, Flavivirus, e.g., Dengue or Zika, and Filoviridae, e.g., an Ebolavirus, e.g., Zaire ebolavirus or Sudan ebolavirus, preferably Zika virus, which are capable of eliciting an immune response against the virus and which, moreover, possess structural properties that minimize or eliminate undesirable properties associated with GP antigens, i.e., the identified antigens induce no or minimal antigen-dependent enhancement (ADE) of infection as a result of eliciting no or fewer infectivity-enhancing antibodies that activate the complement system.

The invention also provides novel antigens identified by such methods, which antigens possess structural homology with an envelope glycoprotein (GP) from a virus associated With antibody-dependent enhancement (ADE) of infection, such as Flaviviridae. e.g., Flavivirus, Dengue or Zika, and Filoviridae, e.g., an Ebolavirus, e.g., Zaire ebolavirus or Sudan ebolavirus, preferably Zika virus and, thus, are capable of eliciting an immune response against the virus, but which preferably induce no or minimal antigen-dependent enhancement (ADE) of infection as a result of eliciting no or fewer infectivity-enhancing antibodies that activate the complement system. Such antigens can be used as the basis for a vaccine to treat or prevent virus infection, preferably Zika, Dengue or Ebola infection.

In one aspect, the invention provides a method of eliciting an immune response by administering an immunologic composition comprising one or more synthetic peptides having an informational spectrum (IS) containing a frequency component F(0.338), where the frequency component may include a range of +/−0.001, 0.002, 0.003, 0.004, or 0.005, e.g., F(0.333-0.343), the amplitude of which is attenuated as compared to the amplitude oldie frequency component F(0.338) contained in the IS of an envelope glycoprotein (GP) protein or fragment thereof of a virus associated with ADE, such as Zika, Dengue, and Ebola viruses, where the attenuation may include at least a 40% reduction in signal strength, e.g., a decrease in amplitude of the peak at F(0.338) by about 40%, about 45%, about 50%, about 55%, about 60%, about 65%, about 70%, about 75%, about 80%, about 85%, about 90%, about 95% or a complete reduction (100%). The synthetic peptide or peptides are capable of eliciting an immune response against the GP protein or fragment thereof.

The GP protein or fragment and the synthetic peptide or peptides may be sufficiently homologous such that the synthetic peptide or peptides is/are suitable for use as an antigen to elicit the production of antibodies, preferably neutralizing antibodies, more preferably neutralizing antibodies without a C1q component, that bind to the GP protein or fragment thereof. In particular, the information spectrum (IS) of the synthetic peptide may contain a frequency component F(0.295), where the frequency component may include a range of +/−0.001, 0.002, 0.003, 0.004, or 0.005, F(0.290-0.300), i.e., a frequency that is conserved across virus. e.g., Zika, envelope glycoproteins proteins and encodes structural information that does not pertain to the interaction between the virus and the host complement system, i.e., C1q.

The synthetic peptide or peptides may have a reduced ability to elicit infectivity-enhancing antibodies, as compared to the ability of the GP protein or fragment thereof to elicit infectivity-enhancing antibodies. Alternatively, the synthetic peptide or peptides may not elicit infectivity-enhancing antibodies.

The synthetic peptide or peptides may induce no or minimal antigen-dependent enhancement (ADE) of infection.

The synthetic peptide or peptides may not interact with a complement protein, such as C1q, or have a reduced ability to interact with a complement protein, such as C1q. As a result, the synthetic peptide does not activate or has a reduced ability to activate the host complement system, which is involved in ADE.

In one aspect, the GP protein or fragment thereof comprises or consists of an amino acid sequence selected from:

```
                                     (SEQ ID NO: 1)
(i)FTCSKKMTGKSIQPENLEYRIMLSVHGSQHSGMIVNDIGHETDENRA
KVEVTPNSPRAEATLGGFGSLGLDCEPRTGLDFSDLYYLTMNNKHWLVHK
EWFHDIPLPWHAGADTGTPHWNNKEALVEFKDAHAKRQTVVVLGSQEGAV
HTALAGALEAEMDGAKGRLFSGHLKCRLKMDKLRLKGVSYSLCTAAFTFT
KVPAETLHGTVTVEVQYAGTDGPCKVPAQMAVDMQTLTPVGRLITANPVI
TESTENSKMMLELDPPFGDSYIVIGVGDKKITHHW;

                                     (SEQ ID NO: 2)
(ii)FTCCKKMPGKSIQPENLEYRIMLPVHGSQHSGMIVNDIGHETDENR
AKVEVTPNSPRAEATLGGFGSLGLDCEPRTGLDFSDLYYLTMNNKHWLVH
KEWFHDIPLPWHAGADTGTPHWNNKEALVEFKDAHAKRQTVVVLGSQEGA
VHTALAGALEAEMDGAKGRLFSGHLKCRLKMDKLRLKGVSYSLCTAAFTF
TKVPAETLHGTVTVEVQSAGTDGPCKVPAQMAVDMQTLTPVGRLITANPV
ITESTENSKMMLELDPPFGDSYIVIGVGDKKITHHW;

                                     (SEQ ID NO: 3)
(iii)FTCSKKMTGKSIQPENLEYRIMLSVHGSQHSGMIVNDIGHETDEN
RAKVEVTPNSPRAEATLGGFGSLGLDCEPRTGLDFSDLYYLTMNNKHRLV
RKEWFHDIPLPWHAGADTGTPHWNNKEALVEFKDAHAKRQTVVVLGSQEG
AVHTALAGALEAEMDGAKGRLFSGHLKCRLKMDKLRLKGVSYSLCTAAFT
FTKVPAETLHGTVTVEVQYAGTDGPCKVPAQMAVDMQTLTPVGRLITANP
VITESTENSKMMLELDPPFGDSYIVIGVGDKKITHHW;

                                     (SEQ ID NO: 4)
(iv)FTCSKKMTGKSIQPENLEYRIMLSVHGSQHSGMIVNDIGHETDENR
AKVEVTPNSPRAEATLGGFGSLGLDCEPRTGLDFSDLYYLTMNNKHWLVH
KEWFHDIPLPWHAGADTGTPHWNNKEALVEFKDAHAKRQTVVVLGSQEGA
VHTALAGALEAEMDGAKGRLFSGHLKCRLKMDKLRLKGVSYSLCTAVCTA
AKVPAETLHGTVTVEVQYAGTDGPCKVPAQMAVDMQTLTPVGRLITANPV
ITESTENSKMMLELDPPFGDSYIVIGVGDKKITHHW;

                                     (SEQ ID NO: 5)
(v)FACSKKMTGKSIQPENLEYRIMLSVHGSQHSGMIVNDTGHETDENRA
KVEITPNSPRAEATLGGFGSLGLDCEPRTGLDFSDLYYLTMNNKHWLVHK
EWFHDIPLPWHAGADTGTPHWNNKEALVEFKDAHAKRQTVVVLGSQEGAV
HTALAGALEAEMDGAKGRLSSGHLKCRLKMDKLRLKGVSYSLCTAAFTFT
KIPAETLHGTVTVEVQYAGTDGPCKVPAQMAVDMQTLTPVGRLITANPVI
TESTENSKMMLELDPPFGDSYIVIGVGEKKITHHW.
```

In another aspect, the GP protein or fragment thereof comprises or consists of an amino acid sequence:

```
                                     (SEQ ID NO: 6)
MGVTGILQLPRDRFKRTSFFLWVIILFQRTFSIPLGVIHNSTLQVSDVDK
LVCRDKLSSTNQLRSVGLNLEGNGVATDVPSVTKRWGFRSGVPPKVVNYE
```

-continued

AGEWAENCYNLEIKKPDGSECLPAAPDGIRGFPRCRYVHKVSGTGPCAGD
FAFHKEGAFFLYDRLASTVIYRGTTFAEGVVAFLILPQAKKDFFSSHPLR
EPVNATEDPSSGYYSTTIRYQATGFGTNETEYLFEVDNLTYVQLESRFTP
QFLLQLNETIYASGKRSNTTGKLIWKVNPEIDTTIGEWAFWETKKNLTRK
IRSEELSFTAVSNGPKNISGQSPARTSSDPETNTTNEDHKIMASENSSAM
VQVHSQGRKAAVSHLTTLATISTSPQPPTTKTGPDNSTHNTPVYKLDISE
ATQVGQHHRRADNDSTASDTPPATTAAGPLKAENTNTSKSADSLDLATTT
SPQNYSETAGNNNTHHQDTGEESASSGKLGLITNTIAGVAGLITGGRRTR
REVIVNAQPKCNPNLHYWTTQDEGAAIGLAWIPYFGPAAEGIYTEGLMHN
QDGLICGLRQLANETTQALQLFLRATTELRTFSILNRKAIDFLLQRWGGT
CHILGPDCCIEPHDWTKNITDKIDQIIHDFVDKTLPDQGDNDNWWTGWRQ
WIPAGIGVTGVIIAVIALFCICKFVF.

The synthetic peptide or peptides may comprise 150-300 amino acids. More particularly, the synthetic peptide or peptides comprise 250-285 amino acids. Even more particularly, the synthetic peptide or peptides comprise or consist of 282 amino acids.

The synthetic peptide or peptides may contain one or more amino acid substitutions relative to the amino acid sequence of the GP protein or fragment thereof. For example, the synthetic peptide or peptides contain 1, 2, 3, 4, 5, 6, 7, 8, 9, or 10 amino acid substitutions relative to the amino acid sequence of the GP protein or fragment thereof. The substitutions attenuate the amplitude of the frequency component F(0.338), which may include a range of +/−0.001, 0.002, 0.003, 0.004, or 0.005, e.g., F(0.333-0.343).

1. In one aspect, the amino acid substitution comprises replacing an amino acid residue in the GP protein or fragment thereof with an amino acid residue having a dissimilar EHP value. For example, the amino acid substitutions may include or consist of replacing an aspartic acid (D) with another amino acid residue, preferably a leucine (L) or an isoleucine (I). Alternatively, the amino acid substitutions may include or consist of replacing a leucine (L) or an isoleucine (I) with an aspartic acid (D). More particularly, the amino acid substitutions may include or consist of one or more of the following: (i) replacing the isoleucine (I) at position 21 of the GP protein with D, M, F, R; (ii) replacing the isoleucine (I) at position 37 of the GP protein with E, V, N, L, G; (iii) replacing the leucine (L) at position 43 of the GP protein with E, I, V, N; (iv) replacing the arginine (R) at position 75 of the GP protein with D, T, S, F; (v) replacing the leucine (L) at position 129 of the GP protein with E, N, G, I, V; (vi) replacing the leucine (L) at position 218 of the GP protein with E, V, I, G; (vii) replacing the leucine (L) at position 240 of the GP protein with D, F, S, R; (viii) replacing the isoleucine (I) at position 266 of the GP protein with E, G, N, L, N, V; and (ix) replacing the isoleucine (I) at position 269 of the GP protein with D, M, T, R. Moreover, the amino acid substitution may include or consist of replacing a leucine (L) with a proline (P), preferably L398P in Ebola GP1 (strain KM233035 in GenBank).

In another aspect, the synthetic peptide or peptides comprise or consist of an amino acid sequence selected from:

(SEQ ID NO: 7)
(i) FACSKKMTGKSIQPENLEYRDMLSVHGSQHSGMIVNETGHETEENRA
KVEITPNSPRAEATLGGFGSLGLDCEPDTGLDFSDLYYLTMNNKHWLVHK
EWFHDIPLPWHAGADTGTPHWNNKEALVEFKRAHAKRQTVVVLGSQEGAV
HTALAGALEAEMDGAKGRLSSGHLKCRDKMDKLRLKGVSYSLCTAAFTFT
KIPAETLHGTVTVEVQYAGTEGPCKVPAQMAVDMQTLTPVGRDITANPVI
TESTENSKMMLELDPPFGESYDVIGVGEKKITHHW;

(SEQ ID NO: 8)
(ii) FACSKKMTGKSIQPENLEYRDMLSVHGSQHSGMIVNVTGHETIENR
AKVEITPNSPRAEATLGGFGSLGLDCEPTTGLDFSDLYYLTMNNKHWLVH
KEWFHDIPLPWHAGADTGTPHWNNKEALVEFKLAHAKRQTVVVLGSQEGA
VHTALAGALEAEMDGAKGRLSSGHLKCRDKMDKLRLKGVSYSLCTAAFTF
TKIPAETLHGTVTVEVQYAGTEGPCKVPAQMAVDMQTLTPVGRFITANPV
ITESTENSKMMLELDPPFGGSYMVIGVGEKKITHHW;

(SEQ ID NO: 9)
(iii) FACSKKMTGKSIQPENLEYRMMLSVHGSQHSGMIVNVTGHETVEN
RAKVEITPNSPRAEATLGGFGSLGLDCEPDTGLDFSDLYYLTMNNKHWLV
HKEWFHDIPLPWHAGADTGTPHWNNKEALVEFKNAHAKRQTVVVLGSQEG
AVHTALAGALEAEMDGAKGRLSSGHLKCRDKMDKLRLKGVSYSLCTAAFT
FTKIPAETLHGTVTVEVQYAGTVGPCKVPAQMAVDMQTLTPVGRSITANP
VITESTENSKMMLELDPPFGNSYTVIGVGEKKITHHW;

(SEQ ID NO: 10)
(iv) FACSKKMTGKSIQPENLEYRFMLSVHGSQHSGMIVNTGHETNENRA
KVEITPNSPRAEATLGGFGSLGLDCEPTTGLDFSDLYYLTMNNKHWLVHK
EWFHDIPLPWHAGADTGTPHWNNKEALVEFKGAHAKRQTVVVLGSQEGAV
HTALAGALEAEMDGAKGRLSSGHLKCRDKMDKLRLKGVSYSLCTAAFTFT
KIPAETLHGTVTVEVQYAGTEGPCKVPAQMAVDMQTLTPVGRDITANPVI
TESTENSKMMLELDPPFGLSYRVIGVGEKKITHHW;

(SEQ ID NO: 11)
(v) FACSKKMTGKSIQPENLEYRRMLSVHGSQHSGMIVNITGHETIENRA
KVEITPNSPRAEATLGGFGSLGLDCEPRTGLDFSDLYYLTMNNKHWLVHK
EWFHDIPLPWHAGADTGTPHWNNKEALVEFKIAHAKRQTVVVLGSQEGAV
HTALAGALEAEMDGAKGRLSSGHLKCRDKMDKLRLKGVSYSLCTAAFTFT
KIPAETLHGTVTVEVQYAGTIGPCKVPAQMAVDMQTLTPVGRRITANPVI
TESTENSKMMLELDPPFGISYRVIGVGEKKITHHW;

(SEQ ID NO: 12)
(vi) FACSKKMTGKSIQPENLEYRMMLSVHGSQHSGMIVNNTGHETIENR
AKVEITPNSPRAEATLGGFGSLGLDCEPDTGLDFSDLYYLTMNNKHWLVH
KEWFHDIPLPWHAGADTGTPHWNNKEALVEFKLAHAKRQTVVVLGSQEGA
VHTALAGALEAEMDGAKGRLSSGHLKCRDKMDKLRLKGVSYSLCTAAFTF
TKIPAETLHGTVTVEVQYAGTGGPCKVPAQMAVDMQTLTPVGRFITANPV
ITESTENSKMMLELDPPFGNSYDVIGVGEKKITHHW;

-continued (SEQ ID NO: 13)
(vii) FACSKKMTGKSIQPENLEYRRMLSVHGSQHSGMIVNNTGHETNEN
RAKVEITPNSPRAEATLGGFGSLGLDCEPSTGLDFSDLYYLTMNNKHWLV
HKEWFHDIPLPWHAGADTGTPHWNNKEALVEFKGAHAKRQTVVVLGSQEG
AVHTALAGALEAEMDGAKGRLSSGHLKCRDKMDKLRLKGVSYSLCTAAFT
FTKIPAETLHGTVTVEVQYAGTVGPCKVPAQMAVDMQTLTPVGRDITANP
VITESTENSKMMLELDPPFGISYDVIGVGEKKITHHW;

(SEQ ID NO: 14)
(viii) FACSKKMTGKSIQPENLEYRDMLSVHGSQHSGMIVNLTGHETIE
NRAKVEITPNSPRAEATLGGFGSLGLDCEPDTGLDFSDLYYLTMNNKHWL
VHKEWFHDIPLPWHAGADTGTPHWNNKEALVEFKLAHAKRQTVVVLGSQE
GAVHTALAGALEAEMDGAKGRLSSGHLKCRDKMDKLRLKGVSYSLCTAAF
TFTKIPAETLHGTVTVEVQYAGTIGPCKVPAQMAVDMQTLTPVGRDITAN
PVITESTENSKMMLELDPPFGISYIVIGVGEKKITHHW;

(SEQ ID NO: 15)
(ix) FACSKKMTGKSIQPENLEYRMMLSVHGSQHSGMIVNGTGHETEENR
AKVEITPNSPRAEATLGGFGSLGLDCEPFTGLDFSDLYYLTMNNKHWLVH
KEWFHDIPLPWHAGADTGTPHWNNKEALVEFKEAHAKRQTVVVLGSQEGA
VHTALAGALEAEMDGAKGRLSSGHLKCRDKMDKLRLKGVSYSLCTAAFTF
TKIPAETLHGTVTVEVQYAGTIGPCKVPAQMAVDMQTLTPVGRRITANPV
ITESTENSKMMLELDPPFGVSYMVIGVGEKKITHHW;

(SEQ ID NO: 16)
(x) FACSKKMTGKSIQPENLEYRFMLSVHGSQHSGMIVNGTGHETGENRA
KVEITPNSPRAEATLGGFGSLGLDCEPTTGLDFSDLYYLTMNNKHWLVHK
EWFHDIPLPWHAGADTGTPHWNNKEALVEFKVAHAKRQTVVVLGSQEGAV
HTALAGALEAEMDGAKGRLSSGHLKCRDKMDKLRLKGVSYSLCTAAFTFT
KIPAETLHGTVTVEVQYAGTLGPCKVPAQMAVDMQTLTPVGRDITANPVI
TESTENSKMMLELDPPFGESYDVIGVGEKKITHHW;

(SEQ ID NO: 17)
(xi) FACSKKMTGKSIQPENLEYRDMLSVHGSQHSGMIVNLTGHETLENR
AKVEITPNSPRAEATLGGFGSLGLDCEPRTGLDFSDLYYLTMNNKHWLVH
KEWFHDIPLPWHAGADTGTPHWNNKEALVEFKNAHAKRQTVVVLGSQEGA
VHTALAGALEAEMDGAKGRLSSGHLKCRDKMDKLRLKGVSYSLCTAAFTF
TKIPAETLHGTVTVEVQYAGTIGPCKVPAQMAVDMQTLTPVGRRITANPV
ITESTENSKMMLELDPPFGISYDVIGVGEKKITHHW;

(SEQ ID NO: 18)
(xii) FACSKKMTGKSIQPENLEYRDMLSVHGSQHSGMIVNITGHETIEN
RAKVEITPNSPRAEATLGGFGSLGLDCEPRTGLDFSDLYYLTMNNKHWLV
HKEWFHDIPLPWHAGADTGTPHWNNKEALVEFKIAHAKRQTVVVLGSQEG
AVHTALAGALEAEMDGAKGRLSSGHLKCRDKMDKLRLKGVSYSLCTAAFT
FTKIPAETLHGTVTVEVQYAGTIGPCKVPAQMAVDMQTLTPVGRDITANP
VITESTENSKMMLELDPPFGISYDVIGVGEKKITHHW.

Additionally, the present invention encompasses an immunologic composition comprising a synthetic peptide or peptides having an informational spectrum (IS) containing a frequency component F(0.338), where the frequency component may include a range of +/−0.001, 0.002, 0.003, 0.004, or 0.005, e.g., F(0.333-0.343), the amplitude of which is attenuated as compared to the amplitude of the frequency component F(0.338) contained in the IS of an envelope glycoprotein (GP) protein or fragment thereof of a virus associated with ADE, e.g., Zika, Dengue and Ebola, preferably the Zika virus envelope glycoprotein (GP) protein or fragment thereof, where the attenuation may include at least a 40% reduction in signal strength, e.g., a decrease in amplitude of the peak at F(0.338) by about 40%, about 45%, about 50%, about 55%, about 60%, about 65%, about 70%, about 75%, about 80%, about 85%, about 90%, about 95% or a complete reduction (100%), wherein the synthetic peptide or peptides are capable of eliciting an immune response against the GP protein or fragment thereof.

The synthetic peptide or peptides employed in the immunologic composition may have no ability or a reduced ability to elicit infectivity-enhancing antibodies, as compared to the ability of the GP protein or fragment thereof to elicit infectivity-enhancing antibodies; induce no or minimal antigen-dependent enhancement (ADE) of infection; have a reduced ability to interact with a complement protein, such as C1q; be sufficiently homologous to the Zika GP protein or fragment thereof that they are suitable for use as an antigen to elicit the production of antibodies (preferably neutralizing antibodies that, more preferably, also lack a C1q component); have an IS that contains a frequency component F(0.295), where the frequency component may include a range of +/−0.001, 0.002, 0.003, 0.004, or 0.005, e.g., F(0.290-0.300); comprise 150-300 amino acids or, more preferably, 250-285 amino acids or, even more preferably, comprise or consist of 282 amino acids; contain one or more amino acid substitutions (e.g., 1, 2, 3, 4, 5, 6, 7, 8, 9, or 10 amino acid substitutions) relative to the amino acid sequence of the GP protein or fragment thereof (particular sequences of which are set forth above and provided herein), which substitutions attenuate the amplitude of the frequency component F(0.338), as set forth above. Zika virus envelope glycoprotein (GP) protein or fragment thereof, and (ii) produces antibodies that bind to a Zika virus GP protein or fragment thereof.

The synthetic peptide or peptides may have no ability or a reduced ability to elicit infectivity-enhancing antibodies, as compared to the ability of the GP protein or fragment thereof to elicit infectivity-enhancing antibodies; induce no or minimal antigen-dependent enhancement (ADE) of infection, have a reduced ability to interact with a complement protein, such as C1q; be sufficiently homologous to the viral GP protein or fragment thereof that they are suitable for use as an antigen to elicit the production of antibodies (preferably neutralizing antibodies that, more preferably, also lack a C1q component); have an IS that contains a frequency component F(0.295), where the frequency component may include a range of +/−0.001, 0.002, 0.003, 0.004, or 0.005, e.g., F(0.290-0.300); comprise 150-300 amino acids or, more preferably, 250-285 amino acids or, even more preferably, comprise or consist of 282 amino acids; contain one or more amino acid substitutions (e.g., 1, 2, 3, 4, 5, 6, 7, 8, 9, or 10 amino acid substitutions) relative to the amino acid sequence of the GP protein or fragment thereof (particular sequences of which are set forth above and provided herein), which substitutions attenuate the amplitude of the frequency component F(0.338), as set forth above. The synthetic peptide or peptides may be suitable for use as an antigen in an immunologic composition, such as a vaccine, including a polyvalent vaccine.

The present invention further encompasses a method of using at least one synthetic peptide as an immunogen in order to generate antibodies, preferably neutralizing antibodies that, more preferably, lack a C1q component, that specifically bind to an envelope glycoprotein or fragment thereof of a virus associated with ADE, e.g., Zika, Dengue and Ebola, preferably the Zika virus envelope glycoprotein (GP) protein or fragment thereof.

Additionally, the present invention contemplates an isolated nucleic acid encoding the synthetic peptide; a vector containing the nucleic acid, and an isolated cell containing the vector as well as an antibody or antigen binding fragment thereof capable of binding to the synthetic peptide. Moreover, the invention further contemplates a therapeutic method or diagnostic method using the synthetic peptide or the antibody or antigen binding fragment thereof that binds to the synthetic peptide.

Furthermore, the present invention encompasses a method for identifying a peptide that elicits an immune response against an envelope glycoprotein or fragment thereof of a virus associated with ADE, e.g., Zika, Dengue and Ebola, preferably the Zika virus envelope glycoprotein (GP) protein or fragment thereof. The method comprises (1)(i) obtaining an amino acid sequence of an envelope glycoprotein or fragment thereof of a virus associated with ADE, e.g., Zika, Dengue and Ebola (ii) assigning an electron-ion interaction potential (EHP) index value to each amino acid residue contained in the amino acid sequence of the GP protein or fragment (iii) subjecting the resultant EHP index values to discrete Fourier transformation (DEA); (iv) generating an informational spectrum (IS) of the at least one GP protein or fragment based on the EHP index values; (2)(i) obtaining an amino acid sequence of a peptide or peptides; (ii) assigning an EHP index value to each amino acid residue contained in the amino acid sequence of the peptide or peptides; (iii) subjecting the resultant EHP index values to discrete Fourier transformation (DFT); (iv) generating an informational spectrum (IS) of each peptide based on the FHP index values; (3) comparing the IS of the GP protein or fragment generated in (1)(iv) to the IS of the peptide or peptides generated in (2)(iv) and (4) identifying the peptide or peptides whose IS contain a frequency component F(0.338), where the frequency component may include a range of +/−0.001, 0.002, 0.003, 0.004, or 0.005, e.g., F(0.333-0.343), the amplitude of which is attenuated as compared to the amplitude of the frequency component F(0.338) contained in the IS of the GP protein or fragment thereof, as one being capable of eliciting an immune response against the GP protein or fragment. In one aspect, the GP protein or fragment and the synthetic peptide are otherwise homologous.

The method may further include synthesizing at least one of the identified peptides; synthesizing at least one of the identified peptides assessing its immunogenicity or ability to generate antibodies, preferably neutralizing antibodies that, more preferably, lack a C1q component, that specifically bind to said at least one GP protein; and/or producing an immunologic composition comprising at least one of the identified peptides.

The synthetic peptide or peptides may have no ability or a reduced ability to elicit infectivity-enhancing antibodies, as compared to the ability of the GP protein or fragment thereof to elicit infectivity-enhancing antibodies; induce no or minimal antigen-dependent enhancement (ADE) of infection; have a reduced ability to interact with a complement protein, such as C1q; be sufficiently homologous to the Zika GP protein or fragment thereof that they are suitable for use as an antigen to elicit the production of antibodies (preferably neutralizing antibodies that, more preferably, also lack a C1q component); have an IS that contains a frequency component F(0.295), where the frequency component may include a range of +/−1-0.001, 0.002, 0.003, 0.004, or 0.005, e.g., F(0.290-0.300); comprise 150-300 amino acids or, more preferably, 250-285 amino acids or, even more preferably, comprise or consist of 282 amino acids; contain one or more amino acid substitutions (e.g., 1, 2, 3, 4, 5, 6, 7, 8, 9, or 10 amino acid substitutions) relative to the amino acid sequence of the GP protein or fragment thereof (particular sequences of which are set forth above and provided herein), which substitutions attenuate the amplitude of the frequency component F(0.338), as set forth above. The synthetic peptide or peptides may be suitable for use as an antigen in an immunologic composition, such as a vaccine, including a polyvalent vaccine.

The present invention also contemplates a method for the treatment or prevention of Zika virus infection in a subject, comprising administering a therapeutically effective amount of the immunologic composition or a therapeutically effective amount of the synthetic peptide or a therapeutically effective amount of the antibody or antigen binding fragment thereof to the subject in need thereof preferably the treated subject is a human, such that the immunologic composition or the synthetic peptide or the antibody or antigen binding fragment thereof treat or prevent Zika infection in the subject.

DETAILED DESCRIPTION OF THE FIGURES

FIG. 1A shows nonredundant amino acid sequences of envelope glycoproteins (GP1) from Zika virus samples isolated in Brazil during 2014-2015 (AHL43501; AHL43502; AHL43503; AHL43505; AMA12087). The GP1 is a candidate antigen for a Zika vaccine. FIG. 1B shows an ISM-based phylogenetic tree showing the relationship among the nonredundant GP1 from the isolated Zika virus samples (AHL43501; AHL43502; AHL43503, AHL43505; AMA12087). The red boxes indicate the Zika virus isolates that have been subsequently further characterized (AHL43503 and AMA12087).

Figure 2A:
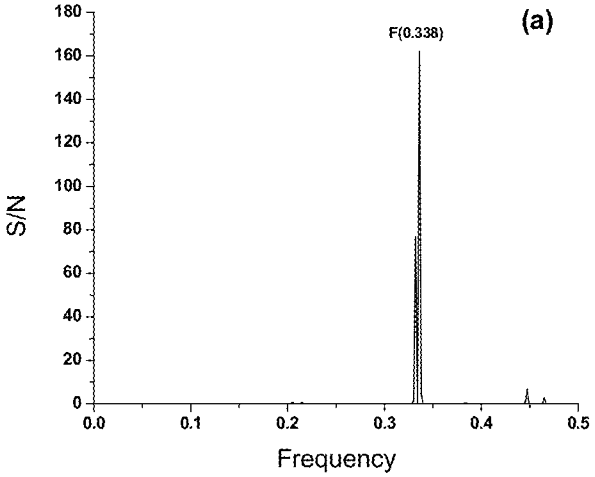
Figure 2B:
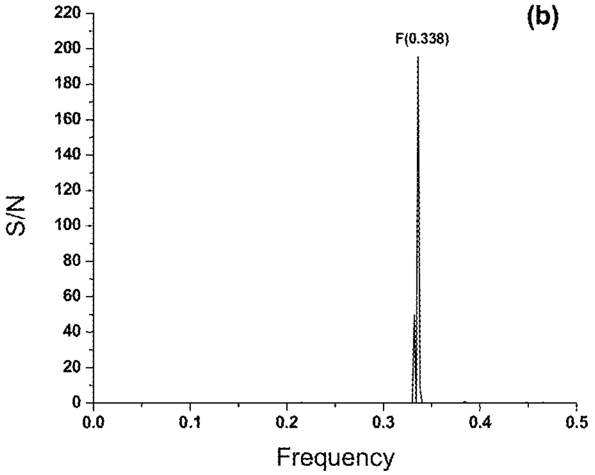
Figure 2C:
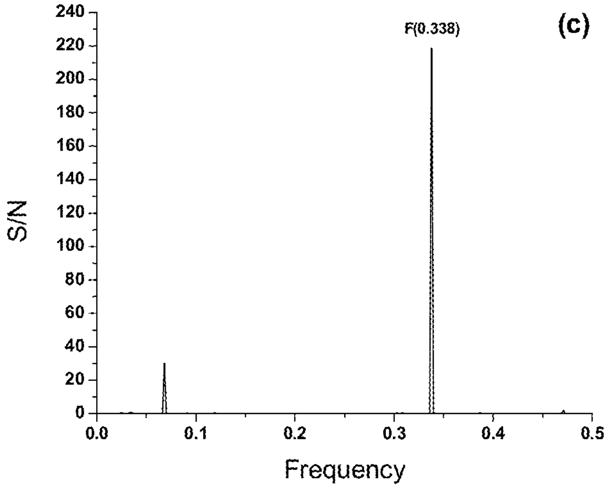

FIG. 2A shows the consensus informational spectrum (CIS) of nonredundant GP1 from Zika viruses isolated in Brazil during 2014-2015 (AHL43501; AHL43502; AHL43503; AHL43505; AMA12087). FIG. 2B shows tile cross-spectrum (CS) between the CIS of Zika GP1 and C1q. FIG. 2C shows the CS between the CIS of Ebola GP1 and C1q. In each panel, the abscissa represents frequencies and the ordinate represents the signal-to-noise ratio (S/N). A frequency component at F(0.338) is a characteristic shared between Zika GP1 and Ebola GP1.

Figure 3A:
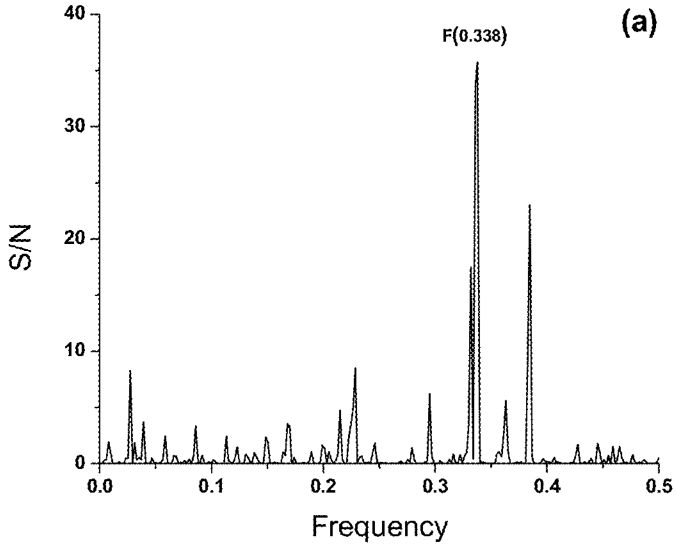
Figure 3B:
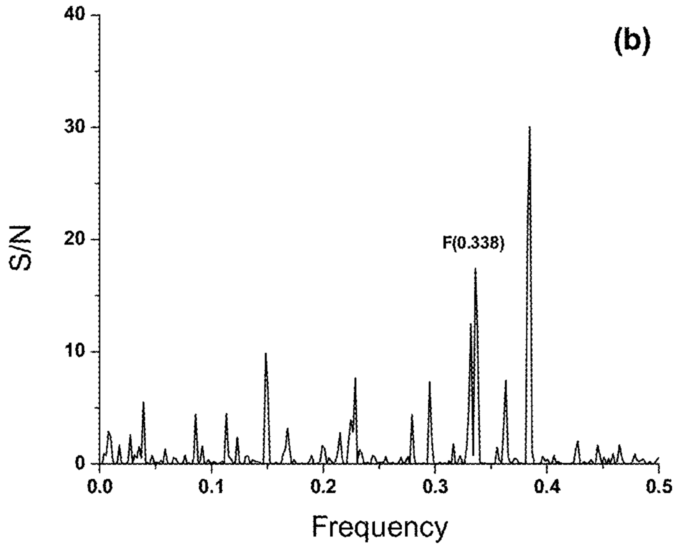

FIG. 3A shows the CIS of C1q and "wild-tape" GP1 from Zika isolates AMA12087 (Brazil 2015) and AHL43503 (Brazil 2014). FIG. 3B shows the CIS of C1q and "modified" GP1 from Zika isolates AMA12087 (Brazil 2015) and AHL43503 (Brazil 2014). The amino acid sequences of GP1 from Zika isolates AMA12087 and AHL43503 were modified (as shown in FIG. 3C), which resulted in attenuated amplitude on the frequency component F(0.338).

Figure 4A:
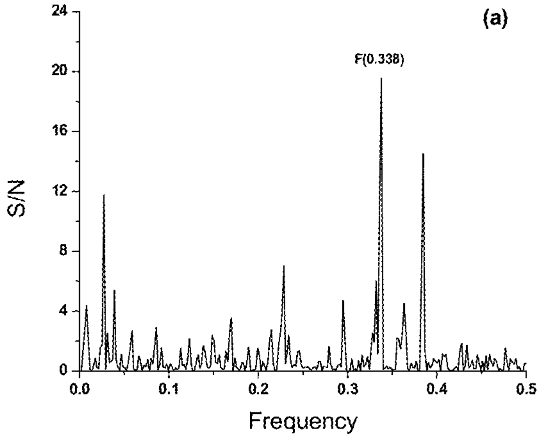
Figure 4B:
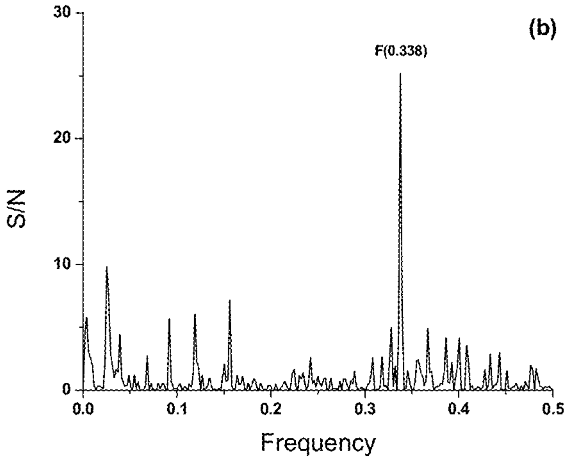
Figure 4C:
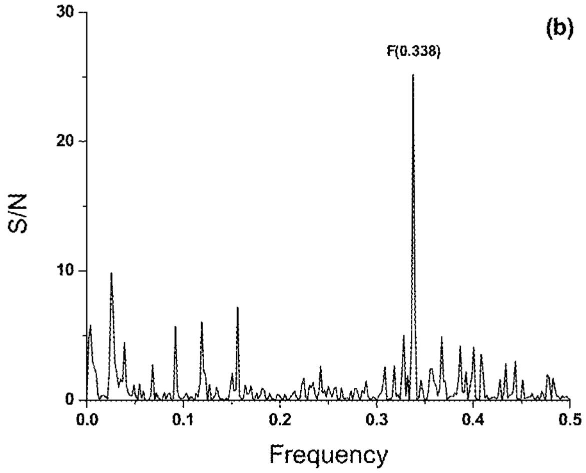

FIG. 4A shows the CS of GP1 proteins from Zika virus and human C1q(c). FIG. 4B shows the CS of GP1 proteins from Ebola vials and human C1q(c). FIG. 4C shows the CS of GP1 proteins from Dengue virus and human C1q(c). In each panel, the abscissa represents frequencies and the ordinate represents the signal-to-noise ratio (S/N).

Figure 5:
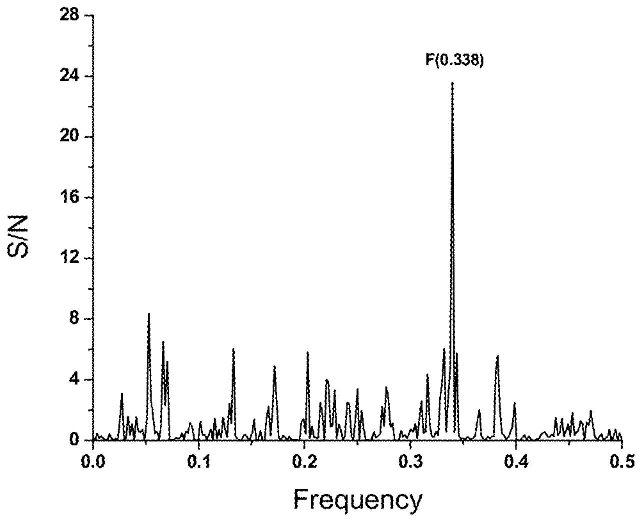

FIG. 5 shows the CS of GP1 proteins from Zika. Ebola and Dengue viruses. The abscissa represents frequencies and the ordinate represents the signal-to-noise ratio (S/N). A frequency component at F(0.338) is a characteristic shared between Zika GP1, Ebola GP1 and Dengue GP1.

Figure 6A:
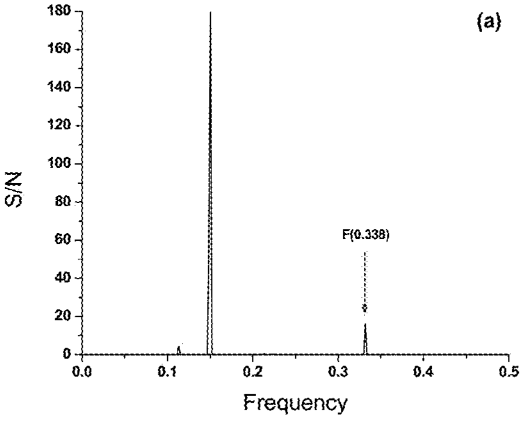
Figure 6B:
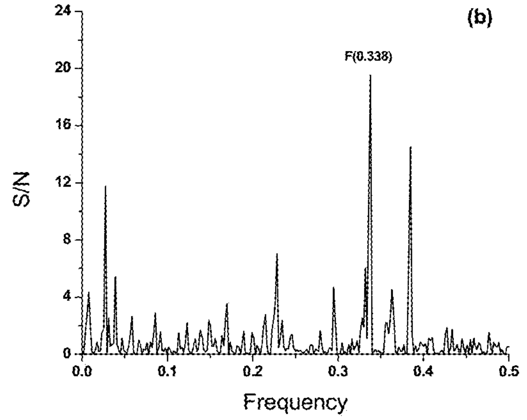
Figure 6C:
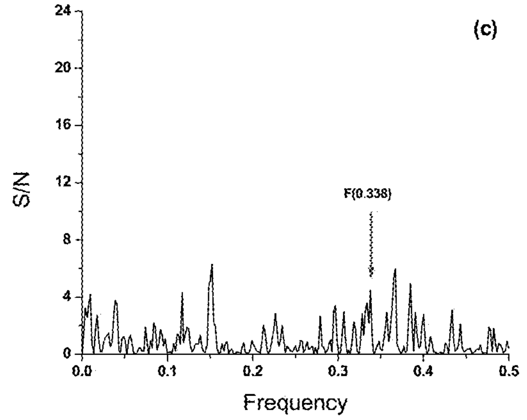

FIG. 6A shows the CIS of twelve (12) GP1 proteins from Zika virus whose amino acid sequence has been modified to attenuate amplitude on the frequency F(0.338). The 12 GP1 proteins correspond to the amino acid sequences described herein as (i)-(xii) and set forth in FIG. 7A and FIG. 7B. FIG. 6B shows the CS of GP1 proteins from Zika virus and human C1q(c). FIG. 6C shows the CS of human C1q(c) and the Zika GP1 protein having the amino acid sequence of (viii), which has been modified to attenuate amplitude on the frequency F(0.338).

FIG. 7A and FIG. 7B shows the amino acid sequences of twelve (12) Zika GP1 proteins that have been modified (relative to the "wild-type" amino acid sequence) to attenuate amplitude on tile frequency F(0.338), which is responsible for GP1 interaction with the complement protein, C1q(c). The red, bolded font indicates an amino acid residue that has been modified, i.e., the amino acid residue present in the "wild-type" sequence of the Zika virus isolate is substituted with a different amino acid residue, preferably an amino acid residue that has a dissimilar EHP value.

Figure 8A:
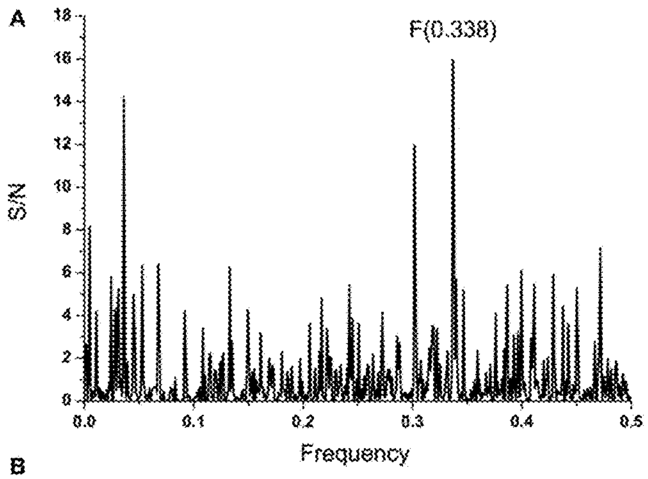
Figure 8B:
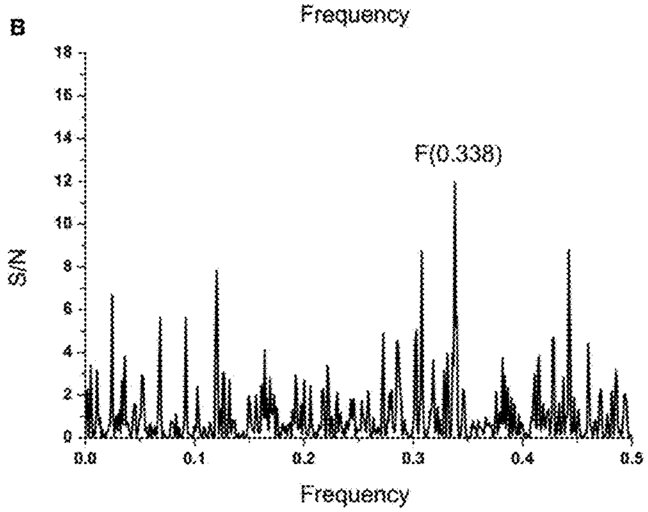
Figure 8C:
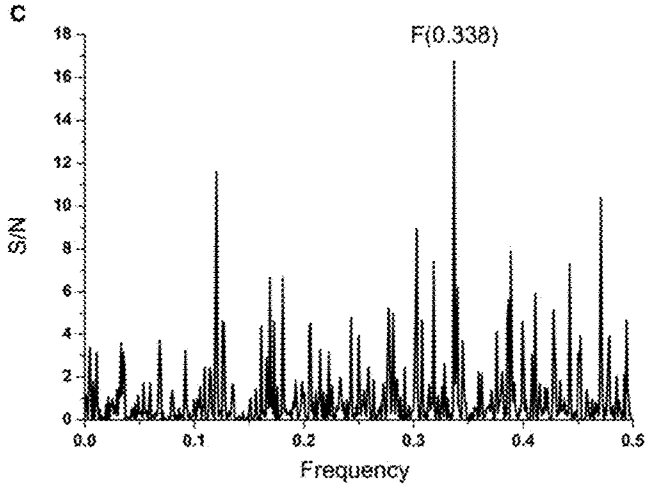

FIG. 8A shows the cross-spectrum (CS) of EMELIN-1 and the GP1 protein from Ebola virus (strain KM233035 in GenBank). FIG. 8B shows the CS of EMELIN-2 and the GP1 protein from Ebola virus (strain KM233035 in GenBank). FIG. 8C shows the CS of EMELIN-3 and the GP1 protein from Ebola virus (strain KM233035 in GenBank). The prominent peak in these spectra is at F(0.338). In each panel, the abscissa represents frequencies and the ordinate represents the signal-to-noise ratio (S/N). These results suggest putative direct interaction or immunological cross-reactivity between Ebola GP1 and EMILINs.

Figure 9A:
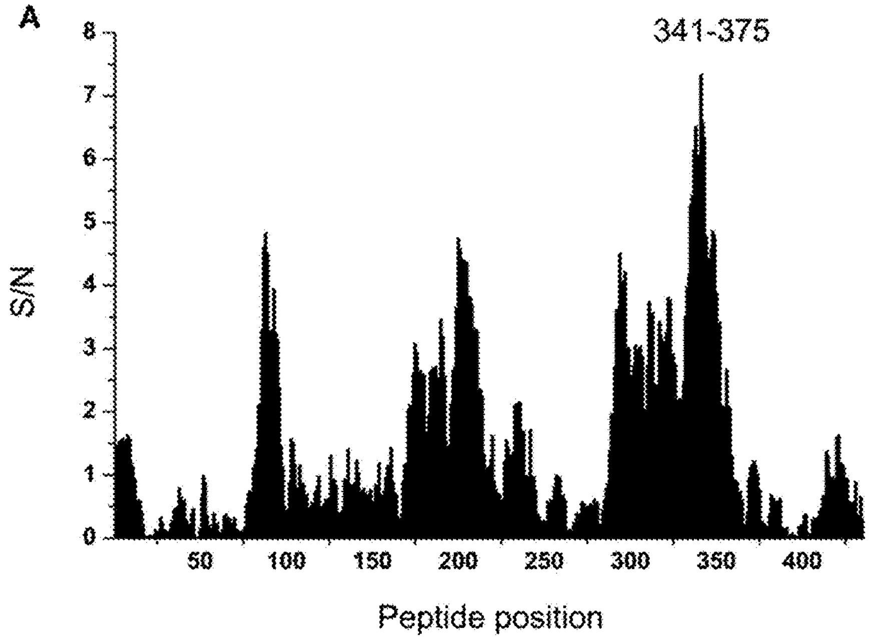
Figure 9B:
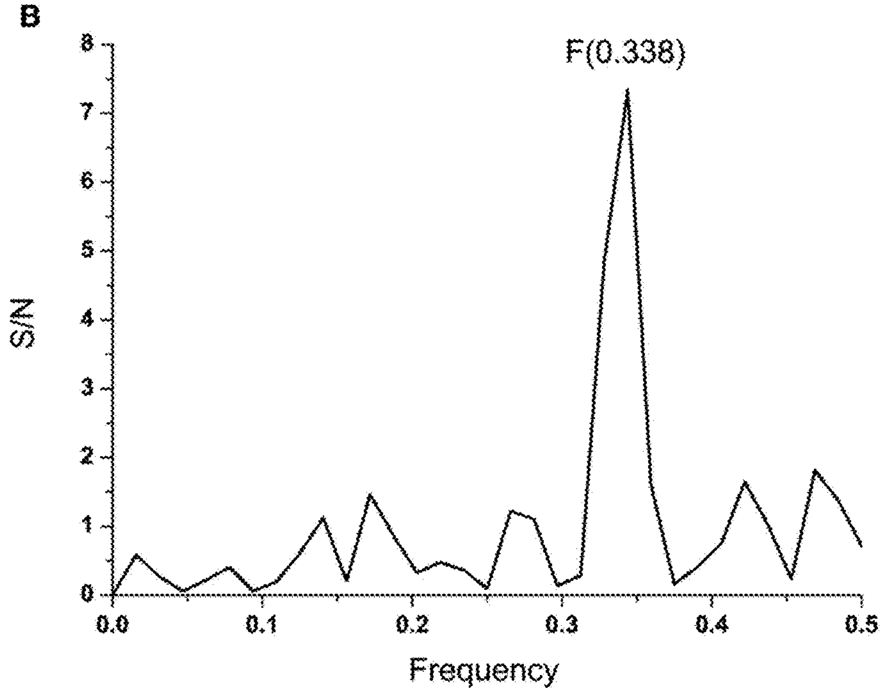

FIG. 9A shows the position of the domain within the GP1 protein from Ebola virus (strain KM233035 in GenBank), i.e., amino acid positions 341-375 (numbering within the mature protein without the 32 amino acid signal peptide), that corresponds to the frequency component F(0.338). FIG. 9B shows the information spectrum (IS) of the domain (resides 341-375).

DETAILED DESCRIPTION OF THE INVENTION

The present invention provides a novel approach to the identification of novel peptides whose EHP structure, but not necessarily sequence, mimic a viral antigenic target (e.g., the envelope glycoprotein) of virus associated with ADE, e.g., Zika, Dengue and Ebola, preferably the Zika virus envelope glycoprotein (GP) protein or fragment thereof, and, thus, can be used to elicit an immune response (e.g., antibody production) against Zika virus. However, the identified antigenic peptides have an attenuated interaction with C1q and/or a reduced ability to activate the complement system, as compared to a viral antigenic target (e.g., the envelope glycoprotein) and, thus, avoid or minimize the adverse effects of a vaccine based thereon (e.g., the identified antigenic peptides do not induce or induce only minimal enhancement of infection).

The EHP structure refers to the electron-ion interaction potential and is unrelated to the linear amino acid sequence (primary structure) and peptide folding motifs (secondary and tertiary structure). In particular, the peptides share EHP homology with at least one viral envelope glycoprotein (GP) protein or fragment thereof and, thus, can be used as an antigen (e.g., in a prophylactic or therapeutic vaccine). As a result of the EHP structural similarity between the identified synthetic peptide and the natural protein, antibodies provided against the synthetic peptide are also capable of recognizing the naturally-occurring viral, e.g., Zika, GP protein. Accordingly, synthetic peptides whose structure mimics that of the viral, e.g., Zika, GP protein can be used to elicit an immune response against infection with the virus while minimizing the undesirable properties associated with tile viral, e.g., Zika, GP protein itself, i.e., the GP protein is characterized, at least in part, by a frequency component of F(0.338) which is responsible for interaction between the virus and the complement system and, thus, may play a role in eliciting infectivity-enhancing antibodies, which are not desirable.

The EHP structure that is used as the basis for peptide selection for this invention relies on the substitution of amino acids occurring within GP1 with amino acids having dissimilar EHP values. The following chart lists the EHP values for the amino acids:

TABLE I

EIIP VALUES FOR 20 AMINO ACIDS

| Amino acid | EIIP Value |
|---|---|
| Leucine | 0.0000 |
| Isoleucine | 0.0000 |
| Asparagine | 0.0036 |
| Glycine | 0.0050 |
| Valine | 0.0057 |
| Glutamic acid | 0.0058 |
| Proline | 0.0198 |
| Histidine | 0.0242 |
| Lysine | 0.0371 |
| Alanine | 0.0373 |
| Tyrosine | 0.0516 |
| Tryptophan | 0.0548 |
| Glutamine | 0.0761 |
| Methionine | 0.0823 |
| Serine | 0.0829 |
| Cysteine | 0.0829 |
| Threoinine | 0.0941 |
| Phenylalanine | 0.0946 |
| Arginine | 0.0959 |
| Aspartic acid | 0.1263 |

Based on the EHP values, the following groupings are used to designate EHP structurally similar peptides. The group L, I, N, G, V, and E (EHP<0.0058) may be interchangeable with one another, and more particularly, the subgroup L, I, N, G, and V (EHP<0.0057) and the subgroup G and E (0.0050≤EHP≤0.0058). The group P, H, K, and A (0.0198≤EHP≤0.0373) may be interchangeable with one another, and more particularly the subgroup P, H, and K (0.0198≤EHP≤0.0371), the subgroup P and H (0.0198≤EHP≤0242), and the subgroup K and A (0.371≤EHP≤0.373). The group Y and W may be interchangeable (0.0516≤EHP≤0.0548). The group Q, M, S, and C (0.0761≤EHP≤0.0829) may be interchangeable. The group T, F, and R (0.0941≤EHP≤0.0959) may be interchangeable. In general, D (EHP=0.1263) is not interchangeable with other amino acids.

The amino acid substitutions employed in the subject invention are "incompatible" in that the substitutions are made across these groups, i.e., not "interchangeable" as set forth herein. For example, "dissimilar" amino acid substitutions may include or consist of replacing D with another amino acid residue, preferably L or I, replacing L or I with D; replacing I with D, M, T, F, or R; replacing R with D, T, S, or F; replacing I, with D, F, S, or R. By substituting an amino acid at a particular position within the naturally-occurring Zika GP protein with a dissimilar amino acid residue, the ability of the Zika GP protein mimic to interact with the complement system C1q) and elicit infectivity-enhancing antibodies is ablated, in whole or in part. The ability of the amino acid substitution(s) to remove or reduce this undesirable property is reflected in a reduction (attenuation) in the amplitude of the frequency component F(0.338).

In particular, the inventors have shown that substituting at least 3, at least 5 or at least 9 amino acid residues within the Zika virus GP1 Zika isolate AMA 12087 obtained in Brazil during 2015) with one or more dissimilar amino acid residues can attenuate the amplitude of the frequency component F(0.338) of the resultant peptide, thereby demonstrating that the "modified" peptide (which maintains sufficient homology with the Zika GP1 such that the synthetic peptide is suitable for use as an antigen to elicit the production of antibodies that bind to the GP protein present in the host following Zika infection) may have reduced interaction with the complement system (such as C1q) and, thus, is less capable of eliciting infectivity-enhancing antibodies, as compared to the ability of the GP protein or fragment thereof to elicit infectivity-enhancing antibodies, or, preferably, does not elicit infectivity-enhancing antibodies and, thereby, induces no or minimal antigen-dependent enhancement (ADE) of infection.

Zika is an emerging global health concern, with 32 countries and territories across various regions currently experiencing active Zika virus transmission. Given its disease-causing potential, particularly birth defects caused thereby, the prevention of Zika infection is a high public health priority. Currently, the most effective single way of protecting people against Zika infection and disease is to avoid traveling to countries where Zika virus is found and/or to avoid mosquito bites (e.g., wearing protective clothing, using insecticides, and/or eliminating mosquito breeding sites).

Zika is a little known emerging mosquito-borne Flavivirus, belonging to the Flaviviridae family that is closely related to the Spondweni serocomplex. Like other members of the *Flavivirus* genus, Zika virus contains a positive single-stranded genomic RNA that encodes, among other things, a structural envelope protein. The envelope glycoprotein (GP), embedded in the membrane and organized as a dimer, allows attachment of the virus particle to the host cell receptor to initiate infection.

Antibodies against the envelope glycoprotein (GP) are likely important for protection against Zika infection. For example, there is a safe and of vaccine against another flavivirus, yellow fever virus, based on the yellow fever F glycoprotein. However, the Zika virus GP has properties that suggest some antibodies specific to this target may enhance viral infectivity. In particular, the envelope glycoprotein from Ebola (and Dengue) are characterized by an informational spectrum (IS) containing a frequency component F(0.338). It has been shown that F(0.338) encodes structural information of the Ebola virus envelope glycoprotein that is responsible for interaction between the virus and the host complement system, i.e., C1q, thereby eliciting antigen-dependent enhancement (ADE) of infection. The inventors showed that introduction of a point mutation (L398R) into the Ebola GP1 attenuated the amplitude of F(0.338). Surprisingly, the inventors discovered that the Zika virus GP is also characterized by an IS containing F(0.338), suggesting that antibodies raised against this antigen may enhance viral infectivity.

In part, based on this observation, the present invention uses an ISM approach, rather than traditional neutralization assays, to identify structural characteristics of Ebola, Dengue, and Zika peptides (e.g., GP1) and, based thereon, obtain novel peptide antigens having a spectral profile overlapping, in part, with the spectral profile of the Ebola, Dengue, and Zika peptide(s), but also differing in that the desired novel peptide antigens have an IS that contains a frequency component F(0.338), the amplitude of which is attenuated (reduced) as compared to the amplitude of the frequency component F(0.338) contained in the IS of the envelope glycoprotein (GP) protein or fragment thereof encoded by an Ebola, Dengue, and Zika virus isolate.

Using this information, the inventors have identified synthetic peptides that differ in amino acid sequence from the naturally-occurring viral. e.g., Zika, peptides but possess the same or similar structural features as the viral protein(s) that are important for interacting with the host cell. As such, these synthetic peptides can be used as a novel antigen(s), e.g., capable of eliciting an immune response against the viral, e.g., Zika, protein or fragment thereof, e.g., suitable for use as an antigen to produce antibodies (preferably, neutralizing antibodies) that bind to the at least one Zika GP protein or fragment thereof. Additionally, because the synthetic peptides contain an IS in which the frequency component F(0.338) has an attenuated (reduced) amplitude as compared to the amplitude of the frequency component F(0.338) contained in the IS of the GP protein or fragment thereof encoded by a Zika vials isolate, the synthetic peptides effectively possess a reduced likelihood of eliciting infectivity-enhancing antibodies as compared to the ability of the GP protein or fragment thereof to elicit infectivity-enhancing antibodies, preferably the synthetic peptides do not elicit infectivity-enhancing antibodies, and/or induce no or minimal antigen-dependent enhancement (ADE) of infection and/or do not interact with a complement protein or have a reduced ability to interact with a complement protein (such as C1q), while retaining the ability to elicit the production of antibodies that bind to the GP protein or fragment thereof. In other words, the identified antigenic peptides mimic the naturally-occurring Zika peptide but without the undesirable properties of the natural peptide.

In the ISM approach, sequences (protein or nucleotide) are transformed into signals by assigning a numerical value to each element (amino acid or nucleotide). These values correspond to the electron-ion interaction potential (EHP), which determines electronic properties of amino acids and nucleotides. The signal obtained is then decomposed into a periodical function by Fourier transformation, resulting in a series of frequencies (F) and their amplitudes (A). The obtained frequencies correspond to the distribution of structural motifs with defined physico-chemical characteristics that are responsible for the biological function of the sequence. In other words, the peak frequencies of IS of a protein sequence reflect its biological or biochemical functions. See Veljkovic et al., Current Medicinal Chemistry (2007) 14:133-135, which is herein incorporated by reference in its entirety.

When comparing proteins that share the same biological or biochemical function(s), this technique allows the detection of code/frequency pairs that are specific for their common biological properties. The method is insensitive to the location of the motifs and, thus, does not require previous alignment of the sequences.

More particularly, it is generally believed that the number of valence electrons and the EHP representing the main energy term of valence electrons are essential physical parameters determining the long-range properties of biological molecules. EHP for organic molecules can be determined by the following simple equation derived from the "general model pseudopotential":

$$W=0.25Z^*\sin(1.04pZ^*)/2\pi$$

where Z* is the average quasi-valence number (AQVN) determined by $$Z^*=\Sigma^m n_i Z_1/N$$

wherein $Z_i$ is the valence number of the i-th atomic component, ni is the number of atoms of the i-th component, m is the number of atomic components in the molecule, and N is the total number of atoms. The EHP values calculated according to equations (1) and (2) are in Rydbergs (Ry). The strong connection between EHP and AQVN of organic molecules and their biological activity has previously demonstrated, e.g., in the context of mutagenicity, carcinogenicity, toxicity, antibiotic activity, and cytostatic activity.

A sequence of N residues is represented as a linear array of N terms, with each term given a weight. The weight assigned to a residue is EHP, determining electronic properties of amino acids and nucleotides, which are responsible for their intermolecular interactions. In this way the alphabetic code of protein or nucleotide sequence is transformed into a sequence of numbers. The obtained numerical sequence, representing the primary structure of protein, is then subjected to a discrete Fourier transformation, which is defined as follows:

$$X(n)=\Sigma x(m)e^{-j(2/N)mn},\ n \text{ is } 1, 2, \ldots, N/2$$

Where x(m) is the m-th member of a given numerical series, N is the total number of points in this series, and X(n) are discrete Fourier transformation coefficients. These coefficients describe the amplitude, phase and frequency of sinusoids, which comprise the original signal. The absolute value of complex discrete Fourier transformation defines the amplitude spectrum and the phase spectrum. The complete information about the original sequence is contained in both spectral functions.

In this way, sequences are analyzed as discrete signals. It is assumed that their points are equidistant with the distance d is 1. The maximal frequency in a spectrum defined in this way is F is ½d is 0.5. The frequency range is independent of the total number of points in the sequence. The total number of points in a sequence influences only the resolution of the spectrum. The resolution of the N-point sequence is 1/n. The n-th point in the spectral function corresponds to a frequency f(n) is of is n/N. Thus, the initial information defined by the sequence of amino acids can now be presented in the form of the informational spectrum (IS), representing the series of frequencies and their amplitudes.

The IS frequencies correspond to distribution of structural motifs with defined physicochemical properties determining a biological function of a protein. When comparing proteins, which share the same biological or biochemical function, the ISM technique allows detection of code/frequency pairs which are specific for their common biological properties, or which correlate with their specific interaction. This common informational characteristic of sequences is determined by a cross-spectrum (CS). A CS of N spectra is obtained by the following equation:

$$C(j)\pi S(i,j)$$

where π (i,j) is the j-th element of the i-th power spectrum and C(j) is the j-th element of CS.

Thus, CS is the Fourier transform of the correlation function for the spectrum. In this way, any spectral component (frequency) not present in all compared informational spectra is eliminated. Peak frequencies in CS are common frequency components for the analyzed sequences. A measure of similarity for each peak is the signal-to-noise ratio (S/N), which represents a ratio between signal intensity at one particular IS frequency and the main value of the whole spectrum. If one calculates the CS for a group of proteins, which have different primary structures, and finds strictly defined peak frequencies, it means that primary structures of the analyzed proteins encode the same information. It was demonstrated that: 1) such a peak exists only for the group of proteins with the same biological function; 2) no significant peak exists for biologically unrelated proteins; 3) peak frequencies are different for different biological functions. Furthermore, it was shown that the proteins and their targets (ligand/receptor, antibody/antigen, etc.) have the same characteristic frequency(ies) in common. Thus, it can be postulated that IS frequencies characterize not only the general function but also recognition and interaction between a particular protein and its target. Once the characteristic frequency for a particular protein function/interaction is identified, it is possible then to utilize the ISM approach to predict the amino acids in the sequence, which essentially contribute to this frequency and are likely to be crucial for the observed function.

The calculation of the IS and CS of the amino acid sequence from Zika virus GP allowed the identification of conserved domains, e.g., structural properties, that likely play a role in the interaction of the viral GP protein with the cellular receptor.

The entry of Zika virus into susceptible cells is mediated, at least in part, by the viral envelope glycoprotein. In the present invention. ISM was applied to identify the spectral properties of GP proteins from Zika virus isolates and, further, to identify undesirable spectral properties of the GP proteins, namely a high amplitude frequency component F(0.338), which is associated with facilitating the interaction between Zika and the complement system, C1q. The ISM was successfully applied in structure-function analysis of different protein sequences, but may also be used in de nova design of peptides.

Using this information, the inventors have identified synthetic peptides that differ in amino acid sequence from the naturally-occurring Zika peptides such that the synthetic peptides lack undesirable traits associated with the naturally-occurring Zika peptides, i.e., induction of ADE, but possess the same or similar structural features as the viral protein(s) that are important for interacting with the host cell. As such, these synthetic peptides can be used as a novel antigen(s), e.g., capable of eliciting an immune response against the Zika GP protein or fragment thereof, e.g., suitable for use as an antigen to produce antibodies (preferably, neutralizing antibodies) that bind to the at least one Zika GP protein or fragment thereof.

The synthetic peptides of the present invention can be administered by different methods, e.g., topically, intranasally, or through parenteral administration, such as through subcutaneous injection, intra-muscular injection, intravenous injection, intraperitoneal injection, or intradermal injection, to a subject in need thereof, e.g., humans, horses, swine, canine and other mammals or avians, etc. The peptides can be used individually or in combination. Additionally, the peptide may be administered alone or as part of a composition that further comprises one or more pharmaceutically acceptable carriers, the proportion of which is determined by the solubility and chemical nature of the peptide, chosen route of administration and standard biological administration. Because inventive peptides may target proteins on the surfaces of the virus and/or the cell, to ensure efficacy, the carrier in such formulations optionally are free or substantially free at least 90, 95, 98, or 99 wt %) of proteins that bind to the peptides.

Suitable pharmaceutically acceptable carriers for the compositions containing the peptides are described in the standard pharmaceutical texts. See, e.g., “Remington's Pharmaceutical Sciences”, 18th Ed., Mack Publishing Company, Easton, Pa. (1990). Specific non-limiting examples of suitable pharmaceutically acceptable carriers include water, saline, dextrose, glycerol, ethanol, or the like and combinations thereof. In addition, if desired, the composition can further contain minor amounts of auxiliary substances such as wetting or emulsifying agents, pH buffering agents that enhance tile antiviral effectiveness of the composition.

Depending on the route of administration, the composition may take the form of a solution, suspension, tablet, pill, capsule, sustained release formulation, powder, cream, lotion, emulsion, or the like.

For topical administration, the antiviral peptide can be formulated into a composition containing an effective amount of the antiviral peptide, typically 0.01 or 0.1 to 10%, of the peptide. Such compositions are typically in the form of a solution, cream, lotion, or emulsion.

For parenteral administration, the peptides of tile present disclosure may be administered by intravenous, subcutaneous, intramuscular, intraperitoneal, or intradermal injection, alone or in compositions further comprising pharmaceutically accepted carriers. For administration by injection, it is preferred to use the antiviral peptide in a solution in a sterile aqueous vehicle which may also contain other solutes such as buffers or preservatives as well as sufficient quantities of pharmaceutically acceptable salts or of glucose to make the solution isotonic. The antiviral peptides of the present disclosure can be obtained in the form of therapeutically acceptable salts that are well-known in the art.

The optimal concentration of the peptide or peptides will necessarily depend upon the specific peptide(s) used, the characteristics oldie patient, and the nature or particular serotype of the virus. These factors can be determined by those of skill in the medical and pharmaceutical arts in view of the present disclosure. In general, the peptides are most desirably administered at a concentration level that will generally afford antiviral effective results against the selected virus(es) without causing any harmful or deleterious side effects. Specific dosages may be adjusted depending on conditions of disease, the age, body weight, general health conditions, sex, diet of the subject, dose intervals, administration routes, excretion rate, and combinations of drugs. Any of the above dosage forms containing effective amounts are well within the bounds of routine experimentation and therefore, well within the scope of the instant disclosure. A therapeutically effective dose may vary depending upon the route of administration and dosage form.

It will be further appreciated that the amount of an antiviral peptide of the present disclosure that is useful will vary not only with the particular peptide selected but also with the route of administration, and the age and condition of the patient, and will ultimately be at the discretion of the attendant physician or veterinarian. In general however, a suitable dose will be in the range of from about 0.01 to 750 mg/kg of body weight per day preferably in the range of 0.1 to 100 mg/kg/day, most preferably in the range of 0.5 to 25 mg/kg/day.

The peptides of the present disclosure may be administered therapeutically or prophylactically. Treatment is preferably commenced before or at the time of infection or at the time the mammal is exposed to a virus that is capable of causing infection, and continued until virus is no longer present or active. However, the treatment can also be commenced post-infection, after the mammal has been exposed to a virus that is capable of causing infection, or after the appearance of established symptoms of infection.

Suitable treatment is given 1-4 times daily and continued for 1-10 days, and typically 8 days post infection. Suitable prophylactic administration is given in single or multiple doses that may be spaced apart in accordance with known booster vaccination schedules and/or given annually.

The desired dose may be presented in a single dose or as divided doses administered at appropriate intervals, for example as two, three, four or more sub-doses per day.

The peptide may be conveniently administered in unit dosage form, for example, containing 10 to 1500 mg, conveniently 20 to 1000 mg, most conveniently 50 to 700 mg of active ingredient per unit dosage form, e.g. 1 mg/kg equates to 75 mg/75 kg of body weight.

The present peptides can also be provided as pharmaceutically acceptable salts. A “pharmaceutically acceptable salt” includes a salt with an inorganic base, organic base, inorganic acid, organic acid, basic amino acid, or acidic amino acid. As salts of inorganic bases, the disclosure includes, for example, alkali metals such as sodium or potassium, alkaline earth metals such as calcium and magnesium or aluminum; and ammonia. As salts of organic bases, the disclosure includes, for example, trimethylamine, triethylamine, pyridine, picoline, ethanolamine, diethanolamine, and triethanolamine. As salts of inorganic acids, the instant disclosure includes, for example, hydrochloric acid, hydroboric acid, nitric acid, sulfuric acid, and phosphoric acid. As salts of organic acids, the instant disclosure includes, for example, formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. As salts of basic amino acids, the instant disclosure includes, for example, arginine, lysine and ornithine. Acidic amino acids include, for example, aspartic acid and glutamic acid.

The following examples are offered to illustrate, but not to limit, the claimed invention.

EXAMPLES

Example 1: Use of ISM to Analyze Human C1q(c) and GP1 Proteins from Zika, Ebola and Dengue Viruses ISM was performed as described above. Generally, the analysis comprised the following steps:

1. each amino acid sequence was converted to the numerical sequence by representing each amino acid with the corresponding value of the EHP;
2. this numerical sequence was converted into a numerical spectrum using fast Fourier transform (FFT), and
3. spectra were mutually compared using cross-spectral analysis with the aim to extract common frequency components.

From the ISM analysis of human C1q(c) and GP1 from the different viruses (see FIG. 4A-C), the frequency component F(0.338) was identified as the dominant peak.

Example 2: Use of ISM to Analyze GP1 Proteins from Zika, Ebola and Dengue Viruses ISM was performed as described above. Generally, the analysis comprised the following steps:

1. each amino acid sequence was converted to the numerical sequence by representing each amino acid with the corresponding value of the EHP;

2. this numerical sequence was converted into a numerical spectrum using fast Fourier transform (FFT), and 3. spectra were mutually compared using cross-spectral analysis with the aim to extract common frequency components.

From the ISM analysis of human C1q(c) and GP1 from the different viruses (see FIG. 5), the cross-spectrum (CS) of GP1 proteins from Zika, Ebola and Dengue viruses share a common frequency component F(0.338).

Example 3: Use of ISM to Analyze the Effects of Point Mutations Introduced into the GP1 Proteins from Zika ISM was performed as described above. Generally, the analysis comprised the following steps:

1. each amino acid sequence was converted to the numerical sequence by representing each amino acid with the corresponding value of the EHP;

2. this numerical sequence was converted into a numerical spectrum using fast Fourier transform (FFT), and 3. spectra were mutually compared using cross-spectral analysis with the aim to extract common frequency components.

From the ISM analysis of Zika virus GP1 modified to contain different point mutations (see FIG. 7), the consensus spectrum generated from the 12 modified Zika GP1 proteins displayed a frequency component F(0.338) (see FIG. 6A) with an attenuated amplitude relative to the amplitude of the frequency component F(0.338) of GP1 proteins obtained from the Zika isolate (see FIG. 6B). This trend is also reflected in the cross-spectrum of human C1q(c) and the modified GP1 protein (referred to herein as (viii)) (see FIG. 6C).

Example 4: Use of ISM to Analyze GP1 Proteins from Ebola and the Effects of Point Mutations Introduced into the GP1 Proteins ISM was performed as described in Veljokvic et al. (Feb. 19, 2015) *In silico analysis suggests interaction between Ebola virus and the extracellular matrix*. Frontiers in Microbiology 6(135):1-11, which is herein incorporated by reference in its entirety. Generally, the analysis comprised the following steps:

1. each amino acid sequence was converted to the numerical sequence by representing each amino acid with the corresponding value of the EHP;

2. this numerical sequence was converted into a numerical spectrum using fast Fourier transform (FFT); and 3. spectra were mutually compared using cross-spectral analysis with the aim to extract common frequency components.

From the ISM analysis of Ebola virus GP1 and elastin microfibrillar interface proteins (EMILINs), the CS of C1q and GP1 of EBOV strains KM233035, representing 99 of 101 GP1 homologous sequences from the outbreak 2014 in GenBank, as well as KJ660346 and KJ660348. This CS is characterized by a single peak corresponding to the IS frequency F(0.338), which represents the common information encoded by primary structures of GP1 and C1q (See FIG. 8A). This result suggests possible cross-reactivity between these proteins, but also their direct mutual interaction. It has been reported that EMILINs, which are predominantly expressed in the ECM, share the C-terminal C1q domain typical of the C1q/TNF superfamily members. The CS of Clqc, representing the major constituent of the human complement subcomponent C1q, and of EMILINs shows that these proteins share dominant information which is represented by the IS frequency F(0.338) (FIG. 8B). The CS of EBOV-2014 GP1 (KM233035) and EMILINs contains the dominant peak at the frequency F(0.338), representing the common information encoded by these viral and human proteins (FIG. 8C). The prominent peaks in CS of EBOVGP1 (KM233035) and EMILIN-1, EMILIN-2 and EMILIN-3 are also at frequency F(0.338) (FIG. 9). These results of FIGS. 8 and 9 suggest putative direct interaction or immunological cross-reactivity between Ebola GP1 and EMILINs.

Example 9: Mapping of the Putative Interacting Sites of Ebola GP1 and EMELINs

The mapping analysis was performed as described in Veljokvic et al. (Feb. 19, 2015) *In silico analysis suggests interaction between Ebola virus and the extracellular matrix*. Frontiers in Microbiology 6(135):1-11, which is herein incorporated by reference in its entirety.

Briefly, to identify the domain which is essential for information corresponding to the IS frequency F(0.338), the computer scanning of the primary structure of Ebola GP1 (KM233035) with peptides of different lengths was performed. This analysis showed that the main contribution to the frequency F(0.3138) comes primarily from the domain 341-375 (a.a. numbering in maturated protein without residues of the signal peptide) (FIG. 9A). According to tile ISM concept, this region of GP1 (denoted VINEBOV1) is essential for possible long-range interaction or immunological crossreactivity between GP1 and EMILINs. Previously, it was shown that domains of proteins which are essential for their long-range interaction overlap their mutual binding site or that they are located in its vicinity (Veljkovic et al. 2009a, b Colombatti et al., 2012; Vergara-Alertetal, 2012). FIG. 9B shows the IS of VIN Ebola containing the dominant peak at the frequency F(0.338).

What is claimed is:

1. A method of inducing an immune response against Zika virus (ZIKV) envelope glycoprotein 1 (GP1) comprising administering to a subject in need thereof a peptide comprising the GP1 sequence of any one of SEQ ID NOS: 1-5, except that the peptide comprises the following amino acid substitutions:

(a) the I at position 21 of the GP1 sequence is replaced with D, M, F or R;

(b) the D at position 37 of the GP1 sequence is replaced with E, V, N, I, L or G;

(c) the D at position 43 of the GP1 sequence is replaced with E, I, V, N, G or L;

(d) the R at position 75 of the GP1 sequence is replaced with D, T, S or F, or is not replaced;

(e) the D at position 129 of the GP1 sequence is replaced with E, L, N, G, I or V;

(f) the D at position 218 of the GP1 sequence is replaced with E, V, I, G or L;

(g) the L at position 240 of the GP1 sequence is replaced with D, F, S or R;

(h) the D at position 266 of the GP1 sequence is replaced with E, G, N, L, I or V; and (i) the I at position 269 of the GP1 sequence is replaced with D, M, T, R or I.

2. The method of claim 1, wherein the peptide comprises any one of SEQ ID NOS: 7-18.

3. The method of claim 2, wherein the peptide comprises SEQ ID NO: 7.

4. The method of claim 2, wherein the peptide comprises SEQ ID NO: 8.

5. The method of claim 2, wherein the peptide comprises SEQ ID NO: 9.

6. The method of claim 2, wherein the peptide comprises SEQ ID NO: 10.

7. The method of claim 2, wherein the peptide comprises SEQ ID NO: 11.

8. The method of claim 2, wherein the peptide comprises SEQ ID NO: 12.

9. The method of claim 2, wherein the peptide comprises SEQ ID NO: 13.

10. The method of claim 2, wherein the peptide comprises SEQ ID NO: 14.

11. The method of claim 2, wherein the peptide comprises SEQ ID NO: 15.

12. The method of claim 2, wherein the peptide comprises SEQ ID NO: 16.

13. The method of claim 2, wherein the peptide comprises SEQ ID NO: 17.

14. The method of claim 1, wherein the peptide comprises SEQ ID NO: 18.

* * * * *